(12) United States Patent
Ikuta et al.

(10) Patent No.: US 7,049,445 B2
(45) Date of Patent: May 23, 2006

(54) BICYCLIC COMPOUNDS

(75) Inventors: Shunichi Ikuta, Shizuoka (JP); Shiro Miyoshi, Shizuoka (JP); Kohei Ogawa, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 263 days.

(21) Appl. No.: 10/761,265

(22) Filed: Jan. 22, 2004

(65) Prior Publication Data

US 2004/0127546 A1 Jul. 1, 2004

Related U.S. Application Data

(62) Division of application No. 10/258,817, filed as application No. PCT/JP01/03575 on Apr. 25, 2001.

(30) Foreign Application Priority Data

Apr. 28, 2000 (JP) .................................. 2000-130414

(51) Int. Cl.
*C07D 209/04* (2006.01)

(52) U.S. Cl. ..................... 548/491; 548/469; 548/490

(58) Field of Classification Search ................ 548/469, 548/490, 491; 514/415
See application file for complete search history.

(56) References Cited

U.S. PATENT DOCUMENTS

| | | | | |
|---|---|---|---|---|
| 3,931,240 | A | * | 1/1976 | Binon et al. ................ 549/466 |
| 4,338,333 | A | | 7/1982 | Ainsworth et al. |
| 4,816,457 | A | | 3/1989 | Baldwin et al. |
| 5,541,197 | A | | 7/1996 | Fisher et al. |
| 5,547,658 | A | * | 8/1996 | Hansenne et al. ............ 424/59 |
| 5,767,133 | A | | 6/1998 | Dow et al. |
| 5,859,044 | A | | 1/1999 | Dow et al. |
| 5,977,124 | A | | 11/1999 | Dow |
| 5,981,572 | A | * | 11/1999 | Ellis et al. .................. 514/456 |
| 6,037,362 | A | | 3/2000 | Miyoshi et al. |
| 6,103,236 | A | * | 8/2000 | Suzawa et al. .......... 424/183.1 |
| 6,172,099 | B1 | | 1/2001 | Miyoshi et al. |
| 6,187,809 | B1 | | 2/2001 | Miyoshi et al. |

FOREIGN PATENT DOCUMENTS

| | | |
|---|---|---|
| DE | 24 29 253 | 1/1976 |
| EP | 0 171 702 | 2/1986 |
| EP | 0 455 006 | 11/1991 |
| EP | 0 659 737 | 6/1995 |
| EP | 1 142 883 | 10/2001 |
| EP | 1 174 425 | 1/2002 |
| EP | 1 238 973 | 9/2002 |
| GB | 1 565 080 | 4/1980 |
| JP | 55-53262 | 4/1980 |
| JP | 58-41860 | 3/1983 |
| JP | 8-165276 | 6/1996 |
| WO | 96/35670 | 11/1996 |
| WO | 97/25311 | 7/1997 |

OTHER PUBLICATIONS

Areschka et al (1973): STN International CAPLUS database, Columbus, Ohio, Accession No., 1974:420780.*
Hansenne et al (1993): STN International CAPLUS database, Columbus, Ohio, Accession No., 1993:656294.*
Barrie C.C. Cantello et al., "BRL 35135," Drugs of the Future, V. 16, 1991, pp. 797–800.
David C. Humber et al., "Disodium(R,R)–5–[2–[[2–(3–Chlorophenyl)–2–hydroxyethyl]–amino]propyl]–1, 3–benzodioxole–2,2–dicarboxylate (CL 316,243)," J. Med Chem., V. 35, 1992, pp. 3081–3084.

* cited by examiner

*Primary Examiner*—Golam M M Shameem
(74) *Attorney, Agent, or Firm*—Young & Thompson

(57) ABSTRACT

Compounds of the general formula (I):

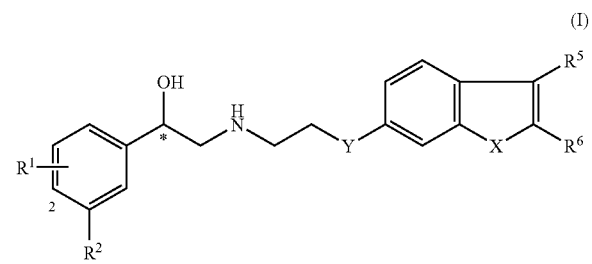

or a salt thereof, wherein $R^1$ is hydrogen, hydroxyl or halogen; $R^2$ is $NHSO_2CH_3$, $SO_2NHCH_3$ or the like; $R^5$ and $R^6$ each independently is hydrogen, $C_{1-6}$ alkyl, optionally substituted phenyl or optionally substituted benzyl; X is NH, sulfur, oxygen or methylene; Y is oxygen, $NR^7$, sulfur, methylene or a bond; and * represents an asymmetric carbon atom. The compounds are useful as a medicine for treating or preventing diabetes, obesity, hyperlipidemia, digestive diseases, depression or urinary disturbances.

3 Claims, No Drawings

BICYCLIC COMPOUNDS

CROSS REFERENCE TO RELATED APPLICATIONS

This application is a division of co-pending application Ser. No. 10/258,817, filed on Oct. 28, 2002. application Ser. No. 10/258,817 is the national phase of PCT International Application No. PCT/JP01/03575 filed on Apr. 25, 2001 under 35 U.S.C. § 371. The entire contents of each of the above-identified applications are hereby incorporated by reference

FIELD OF THE INVENTION

This invention relates to novel compounds which are useful as a medicine for treating and preventing diabetes, obesity, hyperlipidemia, digestive diseases, depression and urinary disturbances.

BACKGROUND OF THE INVENTION

Beta-adrenoreceptors are classified into three classes, β1-adrenoreceptor, β2-adrenoreceptor and β3-adrenoreceptor, and it is recognized that stimulation of β1 induces an increase in the heart rate and stimulation of β2 induces a relaxation of the smooth muscle tissue, thereby resulting in lowering the blood pressure. It is also recognized that stimulation of β3 facilitates the lipolysis in adipocytes, thereby resulting in increasing the thermogenesis. Therefore, compounds having β3-agonist activity were shown to be useful as a medicine for treating and preventing diabetes, obesity and hyperlipidemia (*Nature*, vol. 309, pp. 163–165 (1984); *Int. J. Obes. Relat. Metab. Disord.*, vol. 20, pp. 191–199 (1996); *Drug Development Research*, vol. 32, pp. 69–76 (1994); *J. Clin. Invest.*, vol. 101, pp. 2387–2393 (1998)). Recently, it was shown that β3-adrenoreceptor is expressed in the detrusor and a β3-agonist induces a relaxation of the detrusor (*J. Urinol.*, vol. 161, pp. 680–685 (1999); *J. Pharmacol. Exp. Ther.*, vol. 288, pp. 1367–1373 (1999)).

Some compounds showing a β3-agonist activity have been known. Compounds having high selectivity or having low β1- and β2-stimulating activities are particularly required when their usefulness as a medicine is taken into consideration. This is because compounds having both β1- and β2-stimulating activities induce side effects such as increase in the heart rate and lowering of the blood pressure, as set forth above.

So far, the following compounds have been exemplified as compounds relating to β3:
the compound (BRL 37344) having the following structural formula described in EP 023385 and the literature (*Drugs of the future*, vol. 16, p. 797 (1991)):

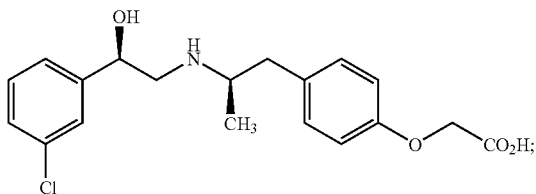

the compound (CL 316,243) having the following structural formula described in EP 0455006 and the literature (*J. Med. Chem.*, vol. 35, p. 3081 (1992)):

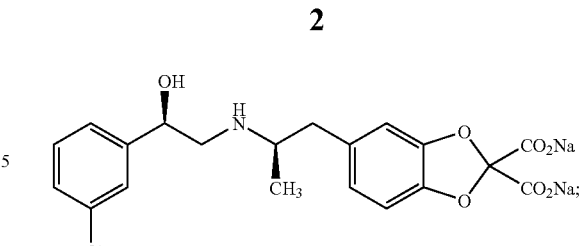

and the compound having the following structural formula described in WO 94/29290:

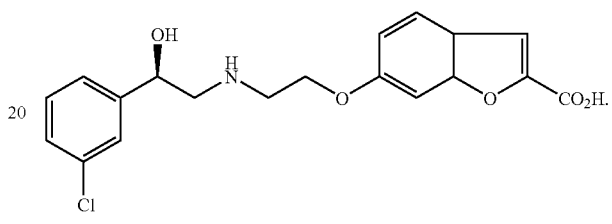

Further, EP 0659737 discloses a variety of compounds and specifically describes as an example in Example 1 in the text of specification the compound having the following structural formula:

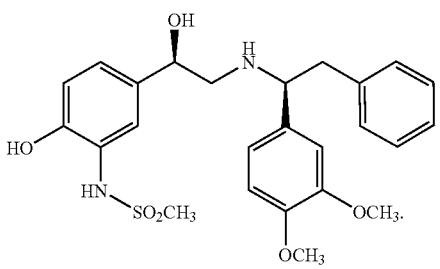

However, the chemical structures of the above compounds are clearly distinct from those of the claimed compounds of the present invention.

In addition, the compound described in EP 171702 and having the following structural formula:

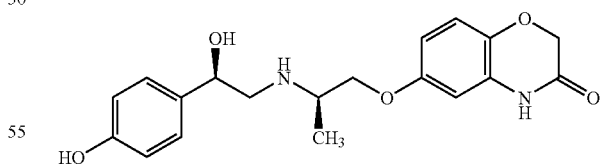

has been known as having heart rate-increasing activity, myocardial contraction enhancement and antiobestic activity. However, this compound acts on the heart and is different from the compounds of the present invention in the chemical structure and in that the former strongly acts on the heart.

Further, the compound described in JP-A-55-53262 and JP-A-58-41860 and having the following structural formula:

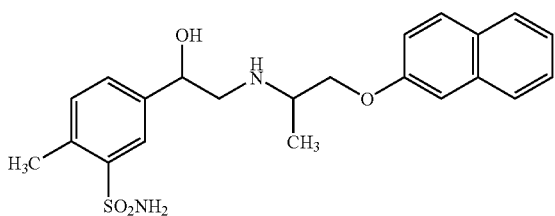

is known as having α,β-blocking activity, namely, the effect of lowering blood pressure; and the compound described in DE 2651572 and having the following structural formula:

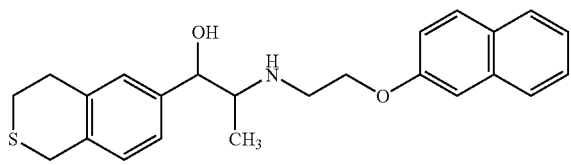

is known as having vasodilator action. However, these compounds are different from the compounds of the present invention in their chemical structures and intended uses.

The present inventors formerly invented compounds having excellent β3-agonist activity and disclosed compounds represented by, for example, the following structural formula in WO 97/25311.

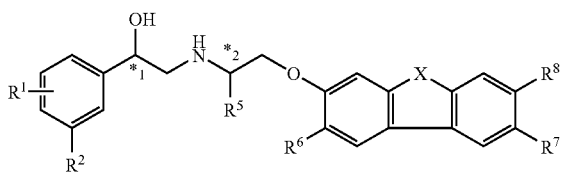

The above compounds, however, are different from the compounds of the present invention in their chemical structures.

SUMMARY OF THE INVENTION

Compounds useful as a medicine for treating or preventing diabetes, obesity, hyperlipidemia, digestive diseases, depression or urinary disturbances are represented by the general formula (I):

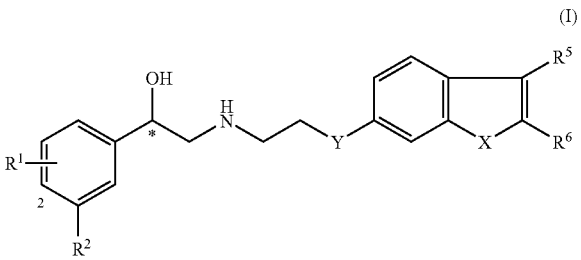

or a salt thereof, wherein $R^1$ is hydrogen, hydroxyl or halogen; $R^2$ is $NHSO_2CH_3$, $SO_2NHCH_3$ or the like; $R^5$ and $R^6$ each independently is hydrogen, $C_{1-6}$ alkyl, optionally substituted phenyl or optionally substituted benzyl; X is NH, sulfur, oxygen or methylene; Y is oxygen, $NR^7$, sulfur, methylene or a bond; and * represents an asymmetric carbon atom.

DISCRIPTION OF PREFERRED EMBODIMENTS

There has been a need for a novel and useful β3-selective agonist which can be used for treating and preventing diabetes, obesity, hyperlipidemia, urinary disturbances and the like.

In order to solve the above problems, the present inventors have found that a novel compound of the general formula (I) set forth below has selective β3-agonist activity.

That is, the present invention relates to a compound of the general formula (I):

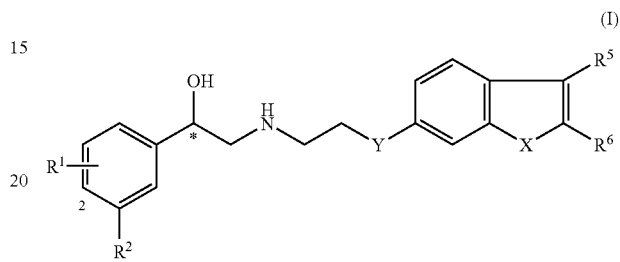

or a salt thereof,
wherein
$R^1$ represents a hydrogen atom, a hydroxyl group or a halogen atom;
$R^2$ represents $NHSO_2R^3$ or $SO_2NR^4R^{4'}$;
$R^3$ represents an alkyl group containing from 1 to 6 carbon atoms, a benzyl group, a phenyl group or $NR^4R^{4'}$;
$R^4$ and $R^{4'}$ may be the same or different and each independently represents a hydrogen atom or an alkyl group containing from 1 to 6 carbon atoms;
$R^5$ and $R^6$ may be the same or different and each independently represents a hydrogen atom, an alkyl group containing from 1 to 6 carbon atoms, an optionally substituted phenyl group or an optionally substituted benzyl group;
X represents NH, a sulfur atom, an oxygen atom or a methylene group;
Y represents an oxygen atom, $NR^7$, a sulfur atom, a methylene group or a bond;
$R^7$ represents a hydrogen atom, an alkyl group containing from 1 to 6 carbon atoms, or an acyl group containing from 1 to 6 carbon atoms; and
* represents an asymmetric carbon atom.

Unless otherwise specified, "a halogen atom" used herein means a fluorine, chlorine, bromine or iodine atom. In addition, "an alkyl group containing from 1 to 6 carbon atoms" means a straight or branched saturated hydrocarbon group containing from 1 to 6 carbon atoms and specifically means methyl, ethyl, n-propyl, i-propyl, n-butyl, i-butyl, sec-butyl, tert-butyl, n-pentyl, i-pentyl, neopentyl, n-hexyl group or the like. Further, "an acyl group containing from 1 to 6 carbon atoms" means a carbonyl group attached to a hydrogen atom or a straight or branched saturated hydrocarbon group containing from 1 to 5 carbon atoms and specifically means formyl, acetyl, propionyl, butanoyl, pentanoyl, hexanoyl group or the like.

$R^1$ represents a hydrogen atom, a hydroxyl group or a halogen atom. Preferred examples thereof include a hydrogen atom, a hydroxyl group, a fluorine atom, a chlorine atom and a bromine atom. Although the position on the benzene ring at which $R^1$ is attached is not limited, the position is preferably ortho- or para-position with respect to the aminoethanol side-chain, with para-position (2-position) being particularly preferred.

$R^2$ represents $NHSO_2R^3$ or $SO_2NR^4R^{4'}$ wherein $R^3$ represents an alkyl group containing from 1 to 6 carbon atoms, a benzyl group, a phenyl group or $NR^4R^{4'}$ and wherein $R^4$ and $R^{4'}$ may be the same or different and each independently represents a hydrogen atom or an alkyl group containing from 1 to 6 carbon atoms. Among the above, particularly preferred examples of $R^2$ include $NHSO_2CH_3$, $SO_2NHCH_3$, $NHSO_2N(CH_3)_2$ and the like.

Within the combinations of $R^1$ and $R^2$, the combination in which $R^1$ is a hydrogen, fluorine, chlorine or bromine atom at para-position (2-position) and $R^2$ is $NHSO_2R^3$ is preferred. The combination in which $R^1$ is a hydroxyl group at para-position (2-position) and $R^2$ is $SO_2NR^4R^{4'}$ is also preferred.

$R^5$ and $R^6$ may be the same or different and represent a hydrogen atom, an alkyl group containing from 1 to 6 carbon atoms, an optionally substituted phenyl group or an optionally substituted benzyl group. Particularly preferably, $R^5$ is a methyl group and $R^6$ is an optionally substituted phenyl group.

The abovementioned substituent which may exist on the benzene ring is a hydroxyl group, a halogen atom, a trifluoromethyl group, a lower alkyl group, a lower alkoxy group, a lower acyl group, NRR', a nitro group and/or a cyano group. R and R' may be the same or different and represent a hydrogen atom, a lower alkyl group, a lower acyl group, a benzyl group or $SO_2R''$. R'' represents a lower alkyl group or a benzyl group. The term "lower" means a straight or branched substituent containing from 1 to 6 carbon atoms. The number of the substituents on the phenyl group is from 1 to 5, preferably from 1 to 2.

X represents NH, an oxygen atom, a sulfur atom or a methylene group, with NH being more preferred.

Y represents an oxygen atom, $NR^7$, a sulfur atom, a methylene group or a bond. In addition, $R^7$ represents a hydrogen atom, an alkyl group containing from 1 to 6 carbon atoms or an acyl group containing from 1 to 6 carbon atoms. Y is preferably an oxygen atom, $NR^7$ or a sulfur atom, more preferably an oxygen atom or NH.

In the general formula (I) set forth above, * is an asymmetric carbon atom, and the compound of the general formula (I) can be in the form of any of two enantiomers, R-enantiomer and S-enantiomer. Not only optically pure isomers, but also mixtures of the two isomers with any mixing ratio are encompassed in the present invention. From the viewpoint of the expression of pharmacological activity, a preferred configuration of the asymmetric carbon * is the configuration R.

In addition, illustrative examples of specific compounds of the general formula (I) of the present invention include the following racemic compounds and optical isomers thereof.

N-[3-[2-[2-(2,3-dimethyl-1H-indol-6-yloxy)ethylamino]-1-hydroxyethyl]phenyl]methanesulfonamide;
N-methyl-[5-[2-[2-(2,3-dimethyl-1H-indol-6-yloxy)ethylamino]-1-hydroxyethyl]-2-hydroxy]benzenesulfonamide;
N-[5-[2-[2-(2,3-dimethyl-1H-indol-6-yloxy)ethylamino]-1-hydroxyethyl]-2-chlorophenyl]methanesulfonamide;
N-[5-[2-[2-(2,3-dimethyl-1H-indol-6-yloxy)ethylamino]-1-hydroxyethyl]-2-fluorophenyl]methanesulfonamide;
N-[3-[2-[2-(3-methyl-2-phenyl-1H-indol-6-yloxy)ethylamino]-1-hydroxyethyl]phenyl]methanesulfonamide;
N-methyl-[5-[2-[2-(3-methyl-2-phenyl-1H-indol-6-yloxy)ethylamino]-1-hydroxyethyl]-2-hydroxy)benzenesulfonamide;
N-[5-[2-[2-(3-methyl-2-phenyl-1H-indol-6-yloxy)ethylamino]-1-hydroxyethyl]-2-chlorophenyl]methanesulfonamide;
N-[5-[2-[2-(3-methyl-2-phenyl-1H-indol-6-yloxy)ethylamino]-1-hydroxyethyl]-2-fluorophenyl]methanesulfonamide;
N-[3-[2-[2-(2-methyl-3-phenyl-1H-indol-6-yloxy)ethylamino]-1-hydroxyethyl]phenyl]methanesulfonamide;
N-methyl-[5-[2-[2-(2-methyl-3-phenyl-1H-indol-6-yloxy)ethylamino]-1-hydroxyethyl]-2-hydroxy]benzenesulfonamide;
N-[5-[2-[2-(2-methyl-3-phenyl-1H-indol-6-yloxy)ethylamino]-1-hydroxyethyl]-2-chlorophenyl]methanesulfonamide;
N-[3-[2-[2-(2,3-dimethylbenzofuran-6-yloxy)ethylamino]-1-hydroxyethyl]phenyl]methanesulfonamide;
N-methyl-[5-[2-[2-(2,3-dimethylbenzofuran-6-yloxy)ethylamino]-1-hydroxyethyl]-2-hydroxy]benzenesulfonamide;
N-[5-(2-[2-(2,3-dimethylbenzofuran-6-yloxy)ethylamino]-1-hydroxyethyl]-2-chlorophenyl]methanesulfonamide;
N-[3-[2-[2-(2,3-dimethylbenzothiophen-6-yloxy)ethylamino]-1-hydroxyethyl]phenyl]methanesulfonamide;
N-methyl-[5-[2-[2-(2,3-dimethylbenzothiophen-6-yloxy)ethylamino]-1-hydroxyethyl]-2-hydroxy]benzenesulfonamide; and
N-[5-[2-[2-(2,3-dimethylbenzothiophen-6-yloxy)ethylamino]-1-hydroxyethyl]-2-chlorophenyl]methanesulfonamide.

Processes for the preparation of compounds represented by the general formula (I) are illustrated in the following.

Preparation Process A

Compounds of the general formula (I) may be prepared according to the processes described in WO 97/25311 and WO 00/58287. That is, an objective compound of the general formula (I) may be prepared by, as the first step, reacting a compound represented by the general formula (II):

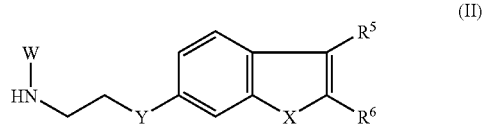

wherein $R^5$, $R^6$, X and Y are as defined above, and W represents a hydrogen atom or an amino-protecting group, with a compound represented by the general formula (III):

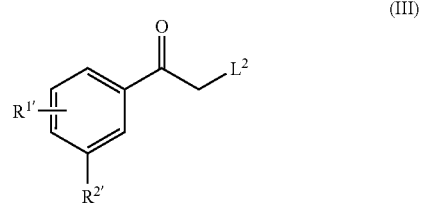

wherein $R^{1'}$ represents a hydrogen atom, $OR^9$ or a halogen atom, $R^9$ represents a hydroxyl-protecting group, $L^2$ represents a leaving group, $R^{2'}$ represents $NW^2$ $SO_2R^3$ or $SO_2NR^4R^{4'}$, $W^2$ represents a hydrogen atom or an amino-protecting group, and $R^3$, $R^4$ and $R^{4'}$ are as defined above, to give an amino ketone ($-CO-CH_2-NW-$) compound; as the second step, reducing the thus obtained amino ketone compound to give an amino alcohol (—CHOH—CH₂—NW—) compound; and, as the final step, optionally removing the hydroxyl-protecting group R⁹ on the benzene ring and, when W and W² are not hydrogen atoms but amino-protecting groups, removing them. Examples of L² include a chlorine atom, a bromine atom, an iodine atom and the like. When W and W² are an amino-protecting group, the amino-protecting group is not limited as long as it is a protecting group used in a common organic synthesis. Preferred examples of the amino-protecting group include a benzyl group, a substituted benzyl group and the like. When R¹' is OR⁹, the hydroxyl-protecting group R⁹ is not limited as long as it is a protecting group used in a common organic synthesis. Preferred examples of the hydroxyl-protecting group include a benzyl group, a substituted benzyl group and the like. The amount of the compound represented by the general formula (II) to be used in the first step is from 1 to 5 mol for 1 mol of the compound represented by the general formula (III). A base may be added to neutralize an acid generated by the reaction. Examples of the base to be used include organic bases such as triethylamine, diisopropylethylamine and pyridine, inorganic bases such as potassium carbonate, sodium hydrogencarbonate and sodium hydroxide and the like. Further, compounds of the general formula (II) may be used also in the form of their salts, provided that the abovementioned base is added. Examples of the solvent to be used in the reaction include lower alcohols such as methanol, ethanol and isopropyl alcohol, chlorinated hydrocarbons such as methylene chloride, chloroform and 1,2-dichloroethane, tetrahydrofuran, dimethylformamide, dimethylsulfoxide and the like, with dimethylformamide being preferred. Although reaction temperature and reaction time are not limited, the reaction is carried out at a temperature of from −30° C. to the boiling point of the selected solvent, preferably a temperature of from 0° C. to 30° C., for 10 minutes to 24 hours. The amino ketone generated in the first step may be used in the reductive reaction of the second step without separation from the reaction mixture. However, the amino ketone may be optionally extracted and purified before the reductive reaction. Examples of the reducing agent to be used include sodium borohydride, sodium cyanoborohydride, borane and the like. Examples of the solvent to be used in the reaction include lower alcohols such as methanol, ethanol and isopropyl alcohol, tetrahydrofuran, dimethylformamide, dimethylsulfoxide, and the like, with ethanol and dimethylformamide being preferred. Although reaction temperature and reaction time are not limited, the reaction is carried out at a temperature of from −30° C. to the boiling point of the selected solvent, preferably a temperature of from 0° C. to 30° C., for 10 minutes to 24 hours. When the removal of the amino-protecting group and/or hydroxyl-protecting group is needed as the final step, they may be removed under reaction conditions usually used for removing the protecting groups to be used. When a benzyl or substituted benzyl group is used as the protecting group, it may be removed, for example, by a hydrogenation reaction using palladium/activated carbon as a catalyst. Compounds represented by the general formula (I), which contain an asymmetric carbon represented by *, are obtained as a racemic mixture by the process set forth above. The racemic mixture can be optically resolved into two optically active substances by converting the racemic mixture to acid addition salts with an optically active acid such as camphorsulfonic acid or mandelic acid followed by a fractional crystallization treatment. The racemic mixture may be also optically resolved using a commercially available optically active column.

Further, optically active substances may be also obtained by carrying out an asymmetric reduction treatment with a hydrogen donating compound in the presence of an asymmetric reduction catalyst in the second step according to the process described in WO 00/58287.

Preparation Process B

In addition, compounds of the general formula (I) may be also prepared by another process set forth below according to the processes described in WO 97/25311 and WO 01/04092. That is, an objective compound of the general formula (I) may be prepared by, as the first step, reacting a compound represented by the formula (II) with a compound represented by the formula (IV):

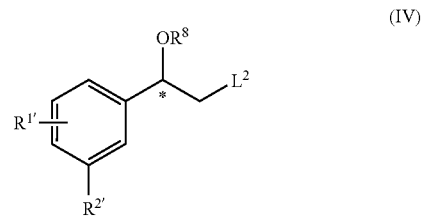

wherein L² represents a leaving group, R⁸ represents a hydroxyl-protecting group, and R¹', R²' and * are as defined above, to give an amino ether (—CHOR⁸—CH₂—NHW—) compound; and, as the second step, removing the hydroxyl-protecting group R⁸, optionally removing the hydroxyl-protecting group R⁹, and when W and W² are not hydrogen atoms but amino-protecting groups, removing them. Examples of L² include a chlorine atom, a bromine atom, an iodine atom and the like, with iodine atom being preferred. W and W² are as set forth above in Preparation Process A. The hydroxyl-protecting group R⁹ when R¹' is OR⁹ is also as set forth above in Preparation Process A. Another hydroxyl-protecting group R⁸ is not limited as long as it is a protecting group used in a common organic synthesis. Preferred examples of the hydroxyl-protecting group include a triethylsilyl group. The amount of the compound represented by the general formula (II) to be used is from 1 to 1.5 mol for 1 mol of the compound represented by the general formula (IV). A base may be added to neutralize an acid generated by the reaction. Examples of the base to be used include triethylamine, diisopropylethylamine and the like. Further, compounds of the general formula (II) may be used also in the form of their salts, provided that the abovementioned base is added. Examples of the solvent to be used in the reaction include dimethylformamide, dimethylacetamide, dimethylsulfoxide and the like, with dimethylformamide being preferred. Although reaction temperature and reaction time are not limited, the reaction is carried out at a temperature of from 0° C. to 90° C., preferably a temperature of 60° C., for 10 minutes to 24 hours. The hydroxyl-protecting group R⁸ and optionally the other protecting groups may be removed under reaction conditions usually used for removing the protecting groups to be used. A triethylsilyl group as R⁸ may be removed using, for example, tetrabutylammonium fluoride. Optically active substances may be prepared as set forth above in Preparation Process A by formation of acid addition salts with an optically active acid followed by a fractional crystallization treatment, or optical resolution using a commercially available optically active column or the like.

Further, an optically active compound represented by the general formula(I) may be also prepared using an optically active compound represented by the general formula (IV) prepared according to the processes described in, for example, WO 97/25311 and WO 01/04092.

Compounds represented by the general formula (III) are known compounds and may be prepared by the process described in, for example, WO 97/25311 or the literature (*J. Med. Chem.*, vol. 10, p. 462 (1966)). Further, compounds represented by the general formula (IV) are known compounds and may be prepared by the process described in, for example, WO 97/25311.

Compounds represented by the general formula (II) are characteristic as important intermediates for synthesizing compounds represented by the general formula (I) and are novel compounds except that both of $R^5$ and $R^6$ represent a hydrogen atom. Processes for the preparation of compounds represented by the general formula (II) are illustrated in the following.

Preparation Process C

Compounds represented by the general formula (II) wherein Y is an oxygen atom may be prepared by the process set forth below. That is, an objective compound may be obtained by reacting a compound represented by the general formula (V):

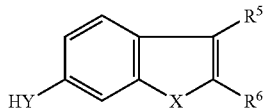

(V)

wherein Y represents an oxygen atom, and $R^5$, $R^6$ and X are as defined above, with a compound represented by the general formula (VI):

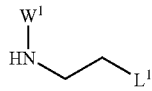

(VI)

wherein $L^1$ represents a leaving group, and $W^1$ represents an amino-protecting group, in the presence of a base; as the second step, removing the amino-protecting group $W^1$; and, as the final step, optionally re-protecting this amino group with another protecting group W. Even if W is a hydrogen atom (i.e. the amino group is in the free form), the compound may be used in the following reaction. Examples of $L^1$ include a chlorine atom, a bromine atom, an iodine atom and the like. The amino-protecting group $W^1$ is not limited as long as it is a protecting group used in a common organic synthesis. Preferred examples include a benzyloxycarbonyl group, a substituted benzyloxycarbonyl group, a tert-butoxycarbonyl group and the like. W may be selected as set forth above in Preparation Process A for compounds of the formula (I). The amount of the compound represented by the general formula (VI) to be used in the first step is from 1 to 5 mol for 1 mol of the compound represented by the general formula (V). Examples of the base to be used include potassium carbonate, sodium carbonate, potassium hydroxide, sodium hydroxide, sodium hydride, sodium methoxide, triethylamine and the like. Examples of the solvent to be used in the reaction include tetrahydrofuran, dimethylformamide, dimethylacetamide, dimethylsulfoxide, acetonitrile and the like. Although reaction temperature and reaction time are not limited, the reaction is carried out at a temperature of from 0° C. to the boiling point of the selected solvent, preferably a temperature of from room temperature to 90° C., for 10 minutes to 24 hours. In the second step, the amino-protecting group $W^1$ may be removed under reaction conditions usually used for removing the protecting group to be used. When a benzyloxycarbonyl or substituted benzyloxycarbonyl group is used as the protecting group, it may be removed, for example, by a hydrogenation reaction using palladium/activated carbon as a catalyst. When a tert-butoxycarbonyl group is used as the protecting group, it may be removed using an acid such as trifluoroacetic acid or hydrochloric acid.

Preparation Process D

Compounds represented by the general formula (II) wherein Y is a sulfur atom may be prepared by the process set forth below. That is, an objective compound may be obtained by reacting a compound represented by the general formula (V):

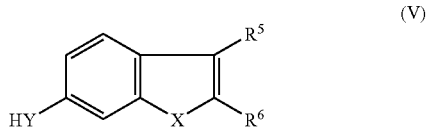

(V)

wherein Y represents a sulfur atom, and $R^5$, $R^6$ and X are as defined above, with a hydrochloride or hydrobromide salt of a compound represented by the general formula (VI):

(VI)

wherein $W^1$ represents a hydrogen atom, and $L^1$ represents a chlorine atom or a bromine atom. The amount of the compound represented by the general formula (VI) to be used is from 1 to 1.5 mol for 1 mol of the compound represented by the general formula (V). The reaction is usually carried out in the presence of a base. Examples of the base include organic bases such as triethylamine, diisopropylethylamine and pyridine, inorganic bases such as potassium carbonate, sodium hydrogencarbonate, sodium hydroxide and the like. Examples of the solvent to be used in the reaction include lower alcohols such as methanol, ethanol and isopropyl alcohol, acetic acid, chlorinated hydrocarbons such as methylene chloride, chloroform and 1,2-dichloroethane, tetrahydrofuran, dimethylformamide, dimethylsulfoxide and the like, which may be used alone or as a mixed solvent comprising plural solvents. Preferably, a mixed solvent of tetrahydrofuran and methanol is used. Although reaction temperature and reaction time are not limited, the reaction is carried out at a temperature of from −30° C. to the boiling point of the selected solvent, preferably a temperature of from 0° C. to 30° C., for 10 minutes to 24 hours.

Preparation Process E

Compounds represented by the general formula (II) wherein Y is $NR^7$ may be prepared by the process set forth below. That is, an objective compound may be obtained by, as the first step, reacting a compound represented by the general formula (V):

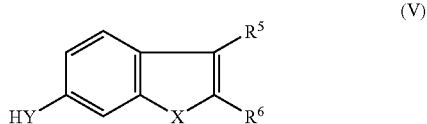

(V)

wherein Y represents NR$^7$, and R$^5$, R$^6$, R$^7$ and X are as defined above, with a compound represented by the general formula (VII):

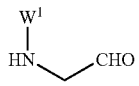

(VII)

wherein W$^1$ represents an amino-protecting group, in the presence of a reducing agent; as the second step, removing the amino-protecting group W$^1$; and, as the final step, optionally re-protecting this amino group with another protecting group W. Even if W is a hydrogen atom (i.e. the amino group is in the free form), the compound may be used in the following reaction. The amino-protecting group W$^1$ is not limited as long as it is a protecting group used in a common organic synthesis. Preferred examples include a benzyloxycarbonyl group, a substituted benzyloxycarbonyl group, a tert-butoxycarbonyl group and the like. W may be selected as set forth above in Preparation Process A for compounds of the formula (I). The amount of the compound represented by the general formula (VII) to be used in the first step is from 1 to 1.5 mol for 1 mol of the compound represented by the general formula (V). Examples of the reducing agent to be used include sodium triacetoxyborohydride, sodium cyanoborohydride, sodium borohydride, lithium cyanoborohydride and the like. Examples of the solvent to be used in the reaction include lower alcohols such as methanol, ethanol and isopropyl alcohol, acetic acid, chlorinated hydrocarbons such as methylene chloride, chloroform and 1,2-dichloroethane, tetrahydrofuran and the like, with tetrahydrofuran being preferred. Although reaction temperature and reaction time are not limited, the reaction is carried out at a temperature of from –30° C. to the boiling point of the selected solvent, preferably a temperature of from 0° C. to 30° C., for 10 minutes to 24 hours. In the second step, the amino-protecting group W$^1$ may be removed under reaction conditions usually used for removing the protecting group to be used. When a benzyloxycarbonyl or substituted benzyloxycarbonyl group is used as the protecting group, it may be removed, for example, by a hydrogenation reaction using palladium/activated carbon as a catalyst. When a tert-butoxycarbonyl group is used as the protecting group, it may be removed using an acid such as trifluoroacetic acid or hydrochloric acid.

Compounds represented by the general formula (II) wherein Y is a methylene group or a bond may be prepared by or according to the known process described in the literature (Troxler et al., *Helv. Chim. Acta.*, vol. 51, p. 1616 (1968)). Further, compounds represented by the general formula (II) wherein Y is a methylene group or a bond may be also prepared according to the known process for preparing indole derivatives, the known process for preparing benzofuran derivatives, the known process for preparing benzothiophene derivatives or the known process for preparing indene derivatives.

Compounds represented by the general formula (V):

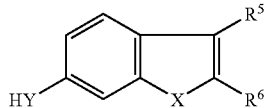

(V)

wherein Y represents NR$^7$, and R$^5$, R$^6$, R$^7$ and X are as defined above may be prepared by or according to the known processes set forth below.

That is, a compound of the formula (V) wherein X=NH, Y=O, R$^5$=H and R$^6$=H may be synthesized by the process described in the literature (Sheppard et al., *J. Med. Chem.*, vol. 37, p. 2011 (1994)). Likewise, a compound of the formula (V) wherein X=NH, Y=O, R$^5$=CH$_3$ and R$^6$=H may be synthesized by the process described in the literature (Ito et al., *J. Am. Chem. Soc.*, vol. 117, p. 1485 (1995)). A compound of the formula (V) wherein X=NH, Y=O, R$^5$=CH$_3$ and R$^6$=CH$_3$ may be synthesized by the process described in the literature (Ockenden et al., *J. Chem. Soc.*, p. 3175 (1957)). A compound of the formula (V) wherein X=NH, Y=O, R$^5$=H and R$^6$=CH$_3$ and a compound of the formula (V) wherein X=O, R$^5$=H and R$^6$=CH$_3$ may be synthesized by the process described in the literature (Baxter et al., *Aust. J. Chem.*, vol. 27, p. 2605 (1974)). A compound of the formula (V) wherein X=NH, Y=O, R$^5$=H and R$^6$=phenyl may be synthesized by the process described in DE-2612057. A compound of the formula (V) wherein X=NH, Y=O, R$^5$=phenyl and R$^6$=H may be synthesized by the process described in the literature (Morton et al., *J. Biol. Chem.*, vol. 179, p. 259 (1949)). A compound of the formula (V) wherein X=NH, Y=O, R$^5$=phenyl and R$^6$=phenyl may be synthesized by the process described in the literature (Teuber et al., *Chem. Ber.*, vol. 91, p. 2089 (1958)). A compound of the formula (V) wherein X=O, Y=O, R$^5$=H and R$^6$=H may be synthesized by the process described in the literature (Foster et al., *J. Chem. Soc.*, p. 2254 (1948)). A compound of the formula (V) wherein X=O, Y=O, R$^5$=CH$_3$ and R$^6$=H may be synthesized by the process described in the literature (Hennings et al., *Tetrahedron Lett.*, vol. 38, p. 6379 (1997)). A compound of the formula (V) wherein X=O, Y=O, R$^5$=CH$_3$ and R$^6$=CH$_3$ may be synthesized by the process described in the literature (Bisagni et al., *Bull. Soc. Chim. Fr.*, p. 925 (1962)). A compound of the formula (V) wherein X=O, Y=O, R$^5$=H and R$^6$=isopropyl may be synthesized by the process described in the literature (Kawase et al., *Bull. Chem. Soc. Japan*, vol. 35, p. 1624 (1962)). A compound of the formula (V) wherein X=O, Y=O, R$^5$=H and R$^6$=phenyl may be synthesized by the process described in the literature (Deschamps et al., *Tetrahedron Lett.*, p. 1109 (1979)). A compound of the formula (V) wherein X=O, Y=O, R$^5$=phenyl and R$^6$=H, a compound of the formula (V) wherein X=O, Y=O, R$^5$=phenyl and R$^6$=CH$_3$, a compound of the formula (V) wherein X=S, Y=O, R$^5$=CH$_3$ and R$^6$=H, and a compound of the formula (V) wherein X=S, Y=O, R$^5$=CH$_3$ and R$^6$=CH$_3$ may be synthesized by the process described in the literature (Royer et al., *Bull. Soc. Chim. Fr.*, p. 942 (1961)). A compound of the formula (V) wherein X=O, Y=O, R$^5$=phenyl and R$^6$=phenyl may be synthesized by the process described in the literature (Hishmat et al., *Indian J. Chem.*, vol. 13, p. 479 (1975)). A compound of the formula (V) wherein X=S, Y=O, R$^5$=H and R$^6$=H may be synthesized by the process described in the literature (Perold et al., *Chem. Ber.*, vol. 92, p. 293 (1959)). A compound of the formula (V) wherein X=S, Y=O, R$^5$=H and R$^6$=phenyl may be synthesized by the process described in the literature (Fries et al., *Justus Liebigs Ann. Chem.*, vol. 527, p. 83 (1937)). A compound of the formula (V) wherein X=S, Y=O, $R^5$=phenyl and $R^6$=phenyl may be synthesized by the process described in the literature (Marcuzzi et al., *Synthesis*, p.451 (1976)). A compound of the formula (V) wherein X=CH$_2$, Y=O, $R^5$=C$_2$H$_5$ and $R^6$=phenyl may be synthesized by the process described in the literature (Anstead et al., *J. Org. Chem.*, vol. 54, p. 1485 (1989)). A compound of the formula (V) wherein X=CH$_2$, Y=O, $R^5$=phenyl and $R^6$=phenyl may be synthesized by the process described in the literature (Anstead et al., *J. Med. Chem.*, vol. 31, p. 1316 (1988)). A compound of the formula (V) wherein X=NH, Y=NH, $R^5$=H and $R^6$=H may be synthesized by the process described in the literature (Yee et al., *J. Med. Chem.*, vol. 33, p. 2437 (1990)). A compound of the formula (V) wherein X=NH, Y=NH, $R^5$=CH$_3$ and $R^6$=CH$_3$ may be synthesized by the process described in the literature (Brown et al., *J. Am. Chem. Soc.*, vol. 74, p. 3934 (1952)). A compound of the formula (V) wherein X=NH, Y=NH, $R^5$=phenyl and $R^6$=CH$_3$ may be synthesized by the process described in the literature (Borshe et al., *Chem. Ber.*, vol. 42, p. 611 (1909)). A compound of the formula (V) wherein X=NH, Y=NH, $R^5$=phenyl and $R^5$=phenyl may be synthesized by the process described in the literature (Kinsley et al., *J. Chem. Soc.*, p. 1 (1958)). A compound of the formula (V) wherein X=O, Y=NH, $R^5$=H and $R^6$=H may be synthesized by the process described in the literature (Gansser et al., *Helv. Chim. Acta.*, vol. 37, p. 437 (1954)). A compound of the formula (V) wherein X=O, Y=NH, $R^5$=CH$_3$ and $R^6$=CH$_3$ may be synthesized by the process described in the literature (Kawase et al., *Bull. Chem. Soc. Japan*, vol. 44, p. 749 (1971)). A compound of the formula (V) wherein X=O, Y=NH, $R^5$=H and $R^6$=phenyl may be synthesized by the process described in the literature (Angeloni et al., *Ann. Chim.*, vol. 55, p. 1028 (1965)). A compound of the formula (V) wherein X=S, Y=NH, $R^5$=H and $R^6$=H may be synthesized by the process described in the literature (Hansch et al., *J. Org. Chem.*, vol. 21, p. 265 (1956)). A compound of the formula (V) wherein X=CH$_2$, Y=NH, $R^5$=H and $R^6$=H may be synthesized by the process described in the literature (Miller et al., *J. Org. Chem.*, vol. 45, p. 5312 (1980)). A compound of the formula (V) wherein X=CH$_2$, Y=NH, $R^5$=CH$_3$ and $R^6$=CH$_3$ may be synthesized by the process described in the literature (Miller et al., *Chem. Ber.*, vol. 23, p. 1885 (1890)). A compound of the formula (V) wherein X=CH$_2$, Y=NH, $R^5$=CH$_3$ and $R^6$=(4-OCH$_3$)phenyl may be synthesized by the process described in the literature (Allen et al., *J. Chem. Soc.*, p. 1045 (1960)). A compound of the formula (V) wherein X=NH, Y=O, $R^5$=CH$_3$ and $R^6$=(4-OCH$_3$)phenyl, and a compound of the formula (V) wherein X=NH, Y=O, $R^5$=CH$_3$ and $R^6$=(3-OCH$_3$)phenyl may be synthesized by the process described in the literature (Angerer et al., *J. Med. Chem.*, p. 1439 (1984)).

The present compounds and the starting compounds and intermediates for preparing each of the present compounds which can be obtained as set forth above may be isolated and purified by the conventional means such as extraction, crystallization, distillation, chromatography, recrystallization or the like.

Salts of a compound of the general formula (I) may be a known salt, and examples thereof include hydrochloride, hydrobromide, sulfate, hydrogensulfate, dihydrogen phosphate, citrate, maleate, tartrate, fumarate, gluconate, methanesulfonate and the like, and acid addition salts with an optically active acid such as camphorsulfonic acid, mandelic acid or substituted mandelic acid. Among them, pharmaceutically acceptable salts are particularly preferred.

When a compound of the general formula (I) is converted into its salt, an acid addition salt of the compound can be obtained by dissolving the compound in alcohol such as methanol or ethanol, to which the equivalent amount to several times amount of the acid component is then added. The acid component to be used may be a pharmaceutically acceptable mineral or organic acid, such as hydrochloric acid, hydrobromic acid, sulfuric acid, hydrogensulfate, dihydrogen phosphate, citric acid, maleic acid, tartaric acid, fumaric acid, gluconic acid or methanesulfonic acid.

Compounds of the present invention and pharmaceutically acceptable salts thereof, which have no recognizable toxic effect, are useful as a medicine. For example, the compounds, which have β3-receptor agonist activities, can be used as a medicine for treating and preventing β3-receptor associated diseases. The term "β3-receptor associated disease" is a generic term directed to diseases which can be improved by agonistic effects mediated by the receptor. Examples of β3-receptor associated diseases include diabetes, obesity, hyperlipidemia, digestive diseases (preferably dyskinesiaof digestive system or ulcer), depression and urinary disturbances.

Even compounds of the present invention and pharmaceutically acceptable salts thereof obtained by a synthetic means have β3-receptor agonistic effects, and those generated as a result of an in vivo metabolism also have the same β3-receptor agonistic effects. Therefore, compounds which generate the present compound as a result of an in vivo metabolism are also useful as a medicine.

A medicine of the present invention is preferably prepared in the form of a pharmaceutical composition by optionally adding a pharmaceutically acceptable carrier to an effective amount of a compound represented by the general formula (I) or a salt thereof. Examples of pharmaceutically acceptable carriers include excipients, binders such as carboxymethylcellulose, disintegrators, lubricants, auxiliaries and the like.

When a compound of the present invention is administered to humans, it can be orally administered in the form of tablet, powder, granule, capsule, sugar-coated tablet, solution, syrup or the like. Further, it can be parenterally administered in the form of injection or the like. The dosage administered will vary dependent on the age and weight of the patient and the extent of disease. The daily dosage for an adult is usually from 0.01 to 2000 mg, which is singly administered or is divided into several dosages and then administered. The administration period can vary between several weeks and several months and the everyday medication is usually applied. However, the daily dosage and administration period can be increased or decreased from the above ranges dependent on the conditions of patient.

The disclosures in the text of specification and/or drawings of Japanese Patent Application No. 2000-130414, from which the present application claims the priority right, are incorporated herein.

The following Examples, Reference Examples and Test Examples specifically illustrate this invention but are not intended to limit it in any way.

In the following examples, each analysis was carried out as follows.

(1) Fast Atom Bombardment Mass Spectrum (FAB-MS)

Fast atom bombardment mass spectrum was determined with a JMS-AX500 type mass spectrometer manufactured by JEOL. LTD (Japan) or a JMS-SX102 type mass spectrometer manufactured by JEOL. LTD (Japan). The matrix used was m-nitrobenzyl alcohol.

(2) Liquid Chromatography-Mass Spectrometry (LC-MS)

The mass spectrometer used was a Platform-LC type mass spectrometer manufactured by Micromassm (England). A compound to be analyzed was ionized by erectrospray (ESI) method. The liquid chromatograph used was that manufactured by GILSON (France). The separation column used was Mightysil RP-18 GP 50-4.6 (product number 25468-96) manufactured by KANTO KAGAKU (Japan). The eluting conditions are as follows.

Flow rate: 2 mL/min;

Solvent:

Liquid A=water containing 0.1% (v/v) acetic acid;

Liquid B=acetonitrile containing 0.1% (v/v) acetic acid;

A linear gradient of 5–100% (v/v) Liquid B over 5 minutes (from 0 to 5 min) was used.

Elution time was indicated by "minute".

(3) Proton Nuclear Magnetic Resonance ($^1$H-NMR) Spectrum

The determination of proton nuclear magnetic resonance spectrum was carried out using a Gemini-300 type nuclear magnetic resonance apparatus manufactured by Varian (U.S.A.). Tetramethylsilane was used as the internal standard and chemical shift was indicated in δ (ppm). In this connection, the splitting patterns were indicated using the following abbreviations.

| s: singlet; | d: doublet; |
|---|---|
| t: triplet; | quartet: quartet; |
| quintet: quintet; | m: multiplet; |
| dd: double doublet; | dt: double triplet; |
| brs: broad singlet. | |

(4) Thin Layer Chromatography (TLC)

The thin layer chromatography (TLC) used was TLC plate (silica gel 60 $F_{254}$, product number 1,05715) manufactured by Merck (Germany). The detection of a compound was carried out by developing the plate followed by irradiation with UV (254 nm).

(5) Preparative Liquid Chromatography

A purifying process with silica gel column was carried out using silica gel 60 manufactured by Merck (Germany). An objective compound was eluted with a mixed solvent (n-hexane/ethyl acetate or chloroform/methanol).

A purifying process with reversed phase column was carried out using a YMC CombiPrep ODS-A CCAAS05-0520WT type column manufactured by YMC (Japan). An objective compound was eluted by gradient elution using water/acetonitrile (containing 0.1% (v/v) acetic acid). The detailed eluting conditions are as follows.

Flow rate: 20 mL/min;

Solvent:

Liquid A=water containing 0.1% (v/v) trifluoroacetic acid;

Liquid B=acetonitrile containing 0.1% (v/v) trifluoroacetic acid;

From 0 to 1 min: Liquid B was maintained at 5% (v/v).

From 1 to 11 min: A linear gradient of 5–50% (v/v) Liquid B was used.

From 11 to 16 min: A linear gradient of 50–100% (v/v) Liquid B was used.

The following abbreviations are used in Examples set forth below.

DMSO: dimethylsulfoxide

THF: tetrahydrofuran

DMF: dimethylformamide

With respect to intermediates about which no preparing process and reference are described in Examples or Reference Examples, their chemical names and the literatures comprising described therein processes for preparing them are mentioned below.

N-(3-bromoacetylphenyl)methanesulfonamide (Larsen et al., *J. Med. Chem.*, vol. 9, pp. 88–97 (1966));

2-benzyloxy-5-bromoacetyl-N-methylbenzenesulfonamide (JP-A-9-249623);

N-(5-bromoacetyl-2-chlorophenyl)methanesulfonamide (JP-A-9-249623); and

N-(3-bromoacetyl-4-fluorophenyl)methanesulfonamide (WO91/12236).

EXAMPLE 1

Synthesis of 2-(2,3-dimethyl-1H-indol-6-yloxy) ethylcarbamic acid benzyl ester 2,3-Dimethyl-6-methoxy-1H-indole (2.0 g; synthesized by the process reported by Ockenden et al., *J. Chem. Soc.*, pp. 3175–3180 (1957)) was mixed with pyridine hydrochloride (7.91 g; mfd. by KANTO KAGAKU). The resulting mixture was stirred at 200° C. for 15 minutes and then cooled. After adding water (100 mL), the mixture was then extracted with ethyl acetate (100 mL). The organic layer was dried over anhydrous sodium sulfate (10 g). The solvent was distilled off under reduced pressure to yield crude 2,3-dimethyl-6-hydroxy-1H-indole (1.86 g) as a gray crystal.

The thus obtained compound (200 mg), 2-bromoethylcarbamic acid benzyl ester (480 mg; synthesized according to the process described in JP-A-9-249623) and potassium carbonate (343 mg) were suspended in DMF (2 mL), and the mixture was stirred at 80° C. for 3 hours. The reaction mixture was cooled and then poured into water (50 mL). The reaction mixture was extracted with ethyl acetate (50 mL) twice. The organic layer was dried over anhydrous sodium sulfate (5 g) and the solvent was distilled off under reduced pressure. The residue was purified by silica gel column chromatography (99:1 chloroform/methanol) to yield the title compound (214 mg) as a colorless crystal.

$^1$H-NMR (DMSO-$d_6$): δ(ppm) 10.42 (1H, s), 7.49 (1H, t, J=5.3) 7.36–7.28 (5H, m), 7.20 (1H, d, J=8.4), 6.74 (1H, d, J=1.8), 6.58 (1H, dd, J=2.1, 8.7), 5.04 (2H, s), 3.95 (2H, t, J=5.7), 3.38 (2H, quartet, J=5.7), 2.25 (3H, s), 2.10 (3H, d, J=0.6);

TLC (99:1 chloroform/methanol): $R_f$=0.34;

LC-MS: elution time 4.6 minutes;

m/z=337 (M–H)$^-$.

EXAMPLE 2

Synthesis of 2-(2,3-dimethyl-1H-indol-6-yloxy) ethylamine

The compound (202 mg; obtained in Example 1) was dissolved in ethanol (5 mL) and 10% palladium/activated carbon (50 mg) was added. The resulting mixture was stirred overnight under a hydrogen gas at atmospheric pressure at room temperature. Palladium/activated carbon was filtered off and the solvent was distilled off under reduced pressure. The residue was washed with isopropyl ether and dried under reduced pressure to yield the title compound (95 mg) as a colorless crystal.

$^1$H-NMR (DMSO-$d_6$): δ(ppm) 10.55 (1H, s), 8.26 (3H, brs), 7.24 (1H, d, J=8.4), 6.81 (1H, d, J=2.4), 6.65 (1H, dd, J=2.1, 8.7), 4.15 (2H, t, J=5.1), 3.19 (2H, quartet, J=5.1), 2.26 (3H, s), 2.11 (3H, s);

LC-MS: elution time 1.8 minutes;

m/z=205 (MH)$^+$.

REFERENCE EXAMPLE 1

Synthesis of N-(3-acetyl-4-chlorophenyl) methanesulfonamide 1-(5-Amino-2-chlorophenyl)ethanone (411 mg; synthesized by the process reported by Radziejewski et al., *Heterocycles*, vol. 26, pp. 1227–1238 (1987)) was dissolved in toluene (5 mL), and pyridine (235 μL) and methanesulfonyl chloride (225 μL) were added. The resulting mixture was stirred at room temperature for 50 minutes. After adding water (50 mL), the reaction mixture was extracted with ethyl acetate (500 mL). The organic layer was washed with an aqueous 1 N hydrochloric acid solution (50 mL) and saturated brine (50 mL) and then dried over anhydrous sodium sulfate (5 g). The solvent was distilled off under reduced pressure to yield the title compound (595 mg) as a colorless crystal.

$^1$H-NMR (CDCl$_3$): δ(ppm) 7.43–7.33 (3H, m), 7.10 (1H, brs), 3.05 (3H, s), 2.67 (3H, s);

TLC (1:1 n-hexane/ethyl acetate): R$_f$=0.31;

LC-MS: elution time 3.1 minutes;

m/z=246 (M−H)$^−$.

REFERENCE EXAMPLE 2

Synthesis of N-(3-bromoacetyl-4-chlorophenyl) methanesulfonamide

The compound (300 mg; obtained in Reference Example 1) was dissolved in dioxane (5 mL), and bromine (77 μL) was added dropwise with ice-cooling. After stirring at room temperature for 1 hour, the solvent was distilled off under reduced pressure. The residue was washed with a water/ethanol mixture (1:1) and then dried under reduced pressure to yield the title compound (312 mg) as a colorless crystal.

$^1$H-NMR (CDCl$_3$): δ(ppm) 7.46–7.36 (3H, m), 6.90 (1H, brs), 4.52 (2H, s), 3.07 (3H, s);

TLC (4:1 n-hexane/ethyl acetate): R$_f$=0.31;

LC-MS: elution time 3.5 minutes;

m/z=324 (M−H)$^−$.

REFERENCE EXAMPLE 3

Synthesis of N-(3-acetyl-5-aminophenyl) methanesulfonamide

3-Amino-5-nitrobenzophenone (4 g; synthesized by the process reported by Berend et al., *J. Prakt. Chem.*, vol. 69, p. 471 (1904)) was dissolved in pyridine (40 mL), and the temperature was maintained at 50° C. Methanesulfonyl chloride (1.9 mL) was added, followed by stirring for 2 hours. Additional methanesulfonyl chloride (1.7 mL) was added, followed by stirring at 50° C. for 2 hours. The reaction mixture was cooled down to room temperature and then poured into water (200 mL). The deposited precipitation was collected by filtration and dried under reduced pressure to yield N-(3-acetyl-5-nitrophenyl) methanesulfonamide (5.4 g) as a crude product. The whole quantity of the crude product was dissolved in ethanol (40 mL), and zinc dust (20 g) was added. After further adding concentrated hydrochloric acid (2 mL), the mixture was heated to reflux for 4 hours. The reaction mixture was filtered. To the filtrate, ethyl acetate (100 mL) was added. The mixture was washed with water (100 mL) three times and the organic layer was dried over anhydrous magnesium sulfate. The solvent was distilled off under reduced pressure and the residue was purified by silica gel column chromatography (95:5 chloroform/methanol) to yield the title compound (3.9 g).

$^1$H-NMR (DMSO-$d_6$): δ(ppm) 8.27 (1H, brs), 6.96 (1H, m), 6.93 (1H, m), 6.71 (1H, m);

TLC (10:1 chloroform/methanol): R$_f$=0.55;

FAB-MS: m/z=229 (M+H)$^+$.

REFERENCE EXAMPLE 4

Synthesis of N-(3-acetyl-5-chlorophenyl) methanesulfonamide

Sodium nitrite (0.34 g) was added in three portions to concentrated sulfuric acid (3.5 mL). After the addition was completed, the solution was stirred at 70° C. for 10 minutes to dissolve the sodium nitrite completely. The resulting solution was allowed to cool down to room temperature and then a suspension of the compound (1 g; obtained in Reference Example 3) in acetic acid (8 mL) was gradually added with ice-cooling. The resulting mixture was allowed to stand at room temperature for 30 minutes and then stirred at 40° C. for 30 minutes to yield a dark red diazonium salt solution. The diazonium salt solution was gradually added to a solution of cuprous chloride (0.95 g) in concentrated hydrochloric acid (10 mL) at room temperature. After foaming was over, the reaction mixture was stirred at 8° C. for 30 minutes and then allowed to room temperature. Water (60 mL) was added and the mixture was extracted with ethyl acetate (100 mL). The ethyl acetate layer was washed with water (100 mL) three times and dried over anhydrous magnesium sulfate. The solvent was distilled off under reduced pressure. The residue was purified by silica gel column chromatography (98:2 chloroform/methanol) to yield the title compound (350 mg) as a light brown powder.

$^1$H-NMR (DMSO-$d_6$): δ(ppm) 7.72 (1H, m), 7.68 (1H, m), 7.55 (1H, m), 3.13 (3H, s), 2.61 (3H, s);

TLC (10:1 chloroform/methanol): R$_f$=0.60;

FAB-MS: m/z=249 (M+H)$^+$.

REFERENCE EXAMPLE 5

Synthesis of N-(3-acetyl-5-bromophenyl) methanesulfonamide

The procedure of Reference Example 4 was repeated using the compound (1 g; obtained in Reference Example 3) as the starting material except that cuprous bromide (1.5 g) and hydrobromic acid were used instead of cuprous chloride and concentrated hydrochloric acid. An after-treatment according to Reference Example 4 yielded the title compound (350 mg) as a colorless crystal.

$^1$H-NMR (DMSO-$d_6$): δ(ppm) 10.21 (1H, brs), 7.83 (1H, m), 7.73 (1H, m), 7.60 (1H, m), 3.08 (3H, s), 2.57 (3H, s);

TLC (10:1 chloroform/methanol): R$_f$=0.86;

FAB-MS: m/z=293 (M+H)$^+$.

REFERENCE EXAMPLE 6

Synthesis of N-(3-bromoacetyl-5-chlorophenyl) methanesulfonamide

The compound (500 mg; obtained in Reference Example 4) was dissolved in dioxane (10 mL). The temperature was maintained at 50° C. and bromine (0.11 mL) was added. After stirring for 30 minutes, water (50 mL) was added to the mixture, and the mixture was extracted with ethyl acetate (50 mL). The ethyl acetate layer was washed with water (50 mL) twice and then dried over anhydrous magnesium sulfate. The solvent was distilled off under reduced pressure and the residue was purified by silica gel column chromatography (1:2 ethyl acetate/hexane) to yield the title compound (600 mg) as a colorless crystal.

$^1$H-NMR (DMSO-$d_6$): δ(ppm) 10.29 (1H, brs), 7.80 (1H, m), 7.70 (1H, m), 7.50 (1H, m), 4.92 (2H, s), 3.80 (3H, s);

TLC (1:1 n-hexane/ethyl acetate): $R_f$=0.85;

FAB-MS: m/z=328 (M+H)$^+$.

REFERENCE EXAMPLE 7

Synthesis of N-(3-bromoacetyl-5-bromophenyl) methanesulfonamide

The procedure of Reference Example 6 was repeated using the compound (650 mg; obtained in Reference Example 5) as the starting material to yield the title compound (510 mg) as a light-brown powder.

$^1$H-NMR (DMSO-$d_6$): δ(ppm) 10.26 (1H, brs), 7.91 (1H, m), 7.75 (1H, m), 7.63 (1H, m), 4.91 (2H, s), 3.09 (3H, s);

TLC (1:1 n-hexane/ethyl acetate): $R_f$=0.75.

EXAMPLE 3

Synthesis of N-[3-[2-[2-(2,3-dimethyl-1H-indol-6-yloxy)ethylamino]-1-hydroxyethyl]phenyl] methanesulfonamide trifluoroacetate N-(3-Bromoacetylphenyl)methanesulfonamide (15 mg), the compound (31 mg; obtained in Example 2) and triethylamine (7 μL) were added to DMF (1 mL) and the resulting mixture was stirred at room temperature for 1 hour. A solution of sodium borohydride (9.5 mg) in ethanol (1 mL) was then added, followed by stirring at room temperature for 5 hours. The solvent was distilled off under reduced pressure. The residue was washed with dilute aqueous ammonia (1 mL, 2.5% (w/v)) twice, dried under reduced pressure, and purified by reversed phase column chromatography to yield the title compound (4.3 mg) as a colorless crystal.

LC-MS: elution time 2.27 minutes;

m/z=418 (M+H)$^+$.

According to the procedure of Example 3, the compounds (Examples 4–8) of Table 1 were synthesized.

EXAMPLE 9

Synthesis of N-methyl-[5-[2-[2-(2,3-dimethyl-1H-indol-6-yloxy)ethylamino]-1-hydroxyethyl]-2-hydroxy]benzenesulfonamide trifluoroacetate N-Methyl-(2-benzyloxy-5-bromoacetyl) benzenesulfonamide (20 mg), the compound (31 mg; obtained in Example 2) and triethylamine (7 μL) were added to DMF (1 mL), and the resulting mixture was stirred at room temperature for 1 hour. A solution of sodium borohydride (9.5 mg) in ethanol (1 mL) was then added, followed by stirring at room temperature for 5 hours. The solvent was distilled off under reduced pressure. The residue was washed with dilute aqueous ammonia (1 mL, 2.5% (w/v)) twice, dried under reduced pressure, and purified by reversed phase column chromatography to yield N-methyl-[5-[2-[2-(2,3-dimethyl-1H-indol-6-yloxy)ethylamino]-1-hydroxyethyl]-2-benzyloxy]benzenesulfonamide trifluoroacetate (16.5 mg). This compound was dissolved in DMF (0.4 mL). 10% Palladium/activated carbon (10 mg) was added and the mixture was stirred under a hydrogen gas at atmospheric pressure for 3 hours. The palladium/activated carbon was filtered off and the solvent was then distilled off under

TABLE 1

| Ex. | Starting compound (amount mg) | Starting compound (amount mg) | Amount of triethylamine (μL) | Product (yield mg) | LC-MS (m/e) | LC-MS retention time (min) |
|---|---|---|---|---|---|---|
| 4 | N-(5-bromoacetyl-2-chlorophenyl) methanesulfonamide (16 mg) | 2-(2,3-dimethyl-1H-indol-6-yloxy)ethylamine (31 mg) | 7 | N-[5-[2-[2-(2,3-dimethyl-1H-indol-6-yloxy)ethylamino]-1-hydroxyethyl]-2-chlorophenyl]methanesulfonamide trifluoroacetate (7.1 mg) | 452 (M + H)+ | 2.36 |
| 5 | N-(3-bromoacetyl-4-fluorophenyl) methanesulfonamide (16 mg) | 2-(2,3-dimethyl-1H-indol-6-yloxy)ethylamine (31 mg) | 7 | N-[3-[2-[2-(2,3-dimethyl-1H-indol-6-yloxy)ethylamino]-1-hydroxyethyl]-4-fluorophenyl]methanesulfonamide trifluoroacetate (5.9 mg) | 436 (M + H)+ | 2.33 |
| 6 | N-(3-bromoacetyl-4-chlorophenyl) methanesulfonamide (16 mg) | 2-(2,3-dimethyl-1H-indol-6-yloxy)ethylamine (31 mg) | 7 | N-[3-[2-[2-(2,3-dimethyl-1H-indol-6-yloxy)ethylamino]-1-hydroxyethyl]-4-chlorophenyl]methanesulfonamide trifluoroacetate (10.3 mg) | 452 (M + H)+ | 2.43 |
| 7 | N-(5-bromoacetyl-3-chlorophenyl) methanesulfonamide (16 mg) | 2-(2,3-dimethyl-1H-indol-6-yloxy)ethylamine (31 mg) | 7 | N-[5-[2-[2-(2,3-dimethyl-1H-indol-6-yloxy)ethylamino]-1-hydroxyethyl]-3-chlorophenyl]methanesulfonamide trifluoroacetate (6.1 mg) | 452 (M + H)+ | 2.48 |
| 8 | N-(3-bromo-5-bromoacetylphenyl) methanesulfonamide (19 mg) | 2-(2,3-dimethyl-1H-indol-6-yloxy)ethylamine (31 mg) | 7 | N-[5-[2-[2-(2,3-dimethyl-1H-indol-6-yloxy)ethylamino]-1-hydroxyethyl]-3-bromophenyl]methanesulfonamide trifluoroacetate (6.1 mg) | 496 (M + H)+ | 2.52 | reduced pressure to yield the title compound (15.3 mg) as a colorless syrup.

LC-MS: elution time 2.20 minutes;
m/z=434 (M+H)$^+$.

EXAMPLE 10

Synthesis of (R)-N-[5-[2-[2-(2,3-dimethyl-1H-indol-6-yloxy)ethylamino]-1-hydroxyethyl]-2-chlorophenyl]methanesulfonamide hydrochloride (Step A) Synthesis of (R)-N-[5-[2-[2-(2,3-dimethyl-1H-indol-6-yloxy)ethylamino]-1-triethylsilyloxyethyl]-2-chlorophenyl]methanesulfonamide The compound (471 mg; obtained in Example 2) was dissolved in acetonitrile (16 mL), to which (R)-N-[5-[2-iodo-1-(triethylsilyloxy)ethyl]-2-chlorophenyl]methanesulfonamide (960 mg; synthesized according to the process described in WO 97/25311) and potassium carbonate (540 mg) were added. The resulting mixture was heated to reflux for 20 hours. The reaction mixture was filtered and the filtrate was placed under reduced pressure to distill the solvent off. The residue was purified by silica gel column chromatography (100:1–75:1 chloroform/methanol) to yield the title compound (690 mg).

$^1$H-NMR (CDCl$_3$): δ(ppm) 0.51–0.60 (6H, m), 0.89 (9H, t, J=7.7), 2.18 (3H, s), 2.32 (3H, s), 2.74–3.01 (4H, m), 2.94 (3H, s), 3.48 (1H, s), 4.07 (2H, t, J=5.1), 4.83 (1H, dd, J=4.4, 7.1), 6.67 (1H, dd, J=2.2, 8.5), 6.77 (1H, d, J=2.2), 7.12–7.17 (2H, m), 7.30 (1H, d, J=8.6), 7.37 (1H, d, J=8.3), 7.64–7.66 (2H, m);

FAB-MS: m/z=566 (M+H)$^+$.

(Step B) Synthesis of (R)-N-[5-[2-[2-(2,3-dimethyl-1H-indol-6-yloxy)ethylamino]-1-hydroxyethyl]-2-chlorophenyl]methanesulfonamide hydrochloride The compound (640 mg; obtained in the above step A) was dissolved in THF (36 mL), to which acetic acid (0.43 mL) and a solution of 1 M tetra-n-butylammonium fluoride in THF (7.5 mL) were added. After stirring at room temperature for 2 hours, the reaction mixture was diluted with ethyl acetate, and then washed with a saturated aqueous sodium bicarbonate solution (three times) and saturated brine (three times). The organic layer was dried and the solvent was distilled off under reduced pressure. The residue was dissolved in ethanol, to which ethanolic 0.5 N hydrochloric acid was added. After stirring, the solvent was distilled off under reduced pressure. To the residue, chloroform was added. The generated precipitate was collected by filtration and then dried to yield the title compound (381 mg).

$^1$H-NMR (CD$_3$OD): δ(ppm) 2.15 (3H, s), 2.30 (3H, s), 2.99 (3H, s), 3.16–3.55 (4H, m), 4.30 (2H, t, J=6.1), 5.04 (1H, dd, J=2.9, 10.3), 6.72 (1H, dd, J=2.2, 8.5), 6.87 (1H, d, J=2.2), 7.26 (1H, d, J=8.6), 7.31 (1H, dd, J=2.2, 8.2), 7.51 (1H, d, J=8.3), 7.66 (1H, d, J=2.2);

FAB-MS: m/z=452 (M+H)$^+$.

EXAMPLE 11

Synthesis of (R)-N-[3-[2-[2-(2,3-dimethyl-1H-indol-6-yloxy)ethylamino]-1-hydroxyethyl]phenyl]methanesulfonamide hydrochloride (Step A) Synthesis of (R)-N-[3-[2-[2-(2,3-dimethyl-1H-indol-6-yloxy)ethylamino]-1-triethylsilyloxyethyl]phenyl]methanesulfonamide The compound (233 mg; synthesized according to the procedure of the step A of Example 10) was dissolved in ethanol (16 mL). After adding 10% palladium/carbon powder (22 mg), the resulting mixture was stirred under a hydrogen atmosphere at room temperature for 20 hours. The reaction mixture was filtered and the filtrate was placed under reduced pressure to distill the solvent off to yield the title compound (220 mg).

$^1$H-NMR (CDCl$_3$): δ(ppm) 0.50–0.59 (6H, m), 0.88 (9H, t, J=7.7), 2.18 (3H, s), 2.32 (3H, s), 2.77–3.03 (4H, m), 2.94 (3H, s), 4.08 (2H, t, J=5.1), 4.85 (1H, dd, J=4.4, 7.2), 6.70 (1H, dd, J=2.0, 8.5), 6.74 (1H, d, J=2.0), 7.15–7.33 (5H, m), 7.69 (1H, brs);

FAB-MS: m/z=532 (M+H)$^+$.

(Step B) Synthesis (R)-N-[3-[2-[2-(2,3-dimethyl-1H-indol-6-yloxy)ethylamino]-1-hydroxyethyl]phenyl]methanesulfonamide hydrochloride The compound (220 mg; obtained in the above step A) was subjected to a reaction similar to that of the step B of Example 10 to yield the title compound (88.3 mg).

$^1$H-NMR (CD$_3$OD): δ(ppm) 2.15 (3H, s), 2.30 (3H, s), 2.94 (3H, s), 3.19–3.53 (4H, m), 4.30 (2H, t, J=6.1), 4.99–5.05 (1H, m), 6.71 (1H, dd, J=2.2, 8.5), 6.86 (1H, d, J=1.8), 7.18–7.40 (5H, m);

FAB-MS: m/z=418 (M+H)$^+$.

EXAMPLE 12

Synthesis of N-methyl-(R)-[5-[2-[2-(2,3-dimethyl-1H-indol-6-yloxy)ethylamino]-1-hydroxyethyl]-2-hydroxy]benzenesulfonamide hydrochloride (Step A) Synthesis of N-methyl-(R)-[5-[2-[2-(2,3-dimethyl-1H-indol-6-yloxy)ethylamino]-1-triethylsilyloxyethyl]-2-benzyloxy]benzenesulfonamide The compound (306 mg; synthesized in Example 2) was dissolved in acetonitrile (10.4 mL), to which N-methyl-(R)-[5-[2-iodo-1-(triethylsilyloxy)ethyl]-2-benzyloxy]benzenesulfonamide (715 mg; synthesized according to the process described in WO 97/25311) and potassium carbonate (351 mg) were added. The resulting mixture was heated to reflux for 22 hours. The reaction mixture was filtered and the filtrate was placed under reduced pressure to distill the solvent off. The residue was purified by silica gel column chromatography (100:1–75:1 chloroform/methanol) to yield the title compound (237 mg).

$^1$H-NMR (CDCl$_3$): δ(ppm) 0.49–0.58 (6H, m), 0.87 (9H, t, J=7.5), 2.18 (3H, s), 2.31 (3H, s), 2.50 (3H, d, J=5.5), 2.75–3.00 (4H, m), 4.06 (2H, t, J=5.1), 4.67 (1H, d, J=5.3), 4.80–4.86 (1H, m), 5.19 (2H, s), 6.70–6.73 (2H, m), 7.04–7.12 (1H, m), 7.25–7.55 (7H, m), 7.77 (1H, brs), 7.96 (1H, brs).

(Step B) Synthesis of N-methyl-(R)-[5-[2-[2-(2,3-dimethyl-1H-indol-6-yloxy)ethylamino]-1-hydroxyethyl]-2-hydroxy]benzenesulfonamide hydrochloride The compound (234 mg; obtained in the above step A) was dissolved in ethanol (15 mL), to which 10% palladium/carbon powder (50 mg) was added. The resulting mixture was stirred under a hydrogen atmosphere at room temperature for 5 hours. The reaction mixture was filtered and the solvent contained in the filtrate was distilled off under reduced pressure. The residue was dissolved in THF (13 mL), to which acetic acid (0.15 mL) and a solution of 1 M tetra-n-butylammonium fluoride in THF (2.64 mL) were added. The resulting mixture was stirred at room temperature for 2 hours. The reaction mixture was diluted with ethyl acetate and then washed with a saturated aqueous sodium bicarbonate solution (four times) and saturated brine (twice). The organic layer was dried and the solvent was distilled off under reduced pressure. The residue was dissolved in THF, to which ethanolic 0.5 N hydrochloric acid was added. After stirring, the solvent was distilled off under reduced pressure.

To the residue, chloroform was added. The generated precipitate was collected by filtration and dried to yield the title compound (102 mg).

$^1$H-NMR (DMSO-d$_6$): δ(ppm) 2.10 (3H, s), 2.25 (3H, s), 2.39 (3H, s), 3.00–3.50 (4H, m), 4.18–4.25 (2H, m), 4.88–4.95 (1H, m), 6.15 (1H, brs), 6.60–6.68 (1H, m), 6.78–6.90 (2H, m), 7.01–7.04 (1H, m), 7.21–7.24 (1H, m), 7.43–7.67 (1H, m), 7.68–7.70 (1H, m), 10.48 (1H, s);

FAB-MS: m/z=434 (M+H)$^+$.

EXAMPLE 13

Synthesis of (R)-N-[3-[2-[2-(3-methyl-2-phenyl-1H-indol-6-yloxy)ethylamino]-1-hydroxyethyl]phenyl] methanesulfonamide hydrochloride (Step A) Synthesis of 6-hydroxy-3-methyl-2-phenyl-1H-indole 6-Methoxy-3-methyl-2-phenyl-1H-indole (5.00 g; synthesized according to the process described in *Tetrahedron*, vol. 41, p. 4615 (1985)) and pyridine hydrochloride (11.56 g) were stirred at 180° C. for 100 minutes. After the reaction mixture was cooled down to room temperature, ethyl acetate and water were added. After the layers were separated, the organic layer was washed sequentially with aqueous 0.5 N hydrochloric acid and saturated brine, and dried. The solvent was then distilled off under reduced pressure. The residue was purified by silica gel column chromatography to yield the title compound (4.50 g).

$^1$H-NMR (DMSO-d$_6$): δ(ppm) 2.36 (3H, s), 6.54 (1H, dd, J=2.2, 8.5), 6.73 (1H, d, J=2.2), 7.25–7.32 (2H, m), 7.46 (2H, t, J=7.7), 7.58–7.64 (2H, m), 8.95 (1H, s), 10.74 (1H, brs).

(Step B) Synthesis of 6-[2-(N-benzyloxycarbonyl) aminoethoxy]-3-methyl-2-phenyl-1H-indole The compound (2.0 g; obtained in the above step A) was dissolved in N,N-dimethylacetamide (25 mL), to which N-benzyloxycarbonyl-2-bromoethylamine (2.95 g; synthesized according to the process described in JP-A-9-249623) and potassium carbonate (2.47 g) were added. The resulting mixture was stirred at 70° C. for 15.5 hours. After adding water, the reaction mixture was extracted with ether. The organic layer was washed with water and saturated brine and then dried. The solvent was distilled off under reduced pressure. The residue was purified by silica gel column chromatography (99:1 chloroform/methanol) to yield the title compound (2.0 g).

$^1$H-NMR (DMSO-d$_6$): δ(ppm) 2.38 (3H, s), 3.41 (2H, m), 4.01 (2H, t, J=5.5), 5.05 (2H, s), 6.67 (1H, dd, J=2.2, 8.5), 6.84 (1H, d, J=2.2), 7.28–7.52 (9H, m), 7.61–7.65 (2H, m), 10.97 (1H, brs).

(Step C) Synthesis of 6-(2-aminoethoxy)-3-methyl-2-phenyl-1H-indole

The compound (2.0 g; obtained in the above step B) was dissolved in a solution of 30% hydrobromic acid in acetic acid (25 mL), followed by stirring at room temperature for 3 hours. The reaction mixture was diluted with ether and neutralized with an aqueous 5 N sodium hydroxide solution. The organic layer was washed with water and saturated brine and then dried. The solvent was distilled off under reduced pressure to yield the title compound (1.06 g).

$^1$H-NMR (DMSO-d$_6$): δ(ppm) 2.39 (3H, s), 3.25 (2H, m), 4.18 (2H, t, J=5.5), 6.75 (1H, dd, J=2.2, 8.5), 6.91 (1H, d, J=2.2), 7.25–7.68 (6H, m), 8.05 (2H, brs), 11.05 (1H, brs).

(Step D) Synthesis of (R)-N-[3-[2-[2-(3-methyl-2-phenyl-1H-indol-6-yloxy)ethylamino]-1-triethylsilyloxyethyl] phenyl]methanesulfonamide The compound (400 mg; obtained in the above step C) was dissolved in N,N-dimethylacetamide (5 mL), to which (R)-N-[3-(2-iodo-1-triethylsilyloxyethyl)phenyl] methanesulfonamide (752 mg) and diisopropylethylamine (640 mg) were added. The resulting mixture was stirred at 70° C. for 20 hours. The reaction mixture was diluted with water and extracted with ethyl acetate. The organic layer was washed with water and saturated brine and then dried. The solvent was distilled off under reduced pressure. The residue was purified by silica gel column chromatography (99:1–95:5 chloroform/methanol) to yield the title compound (110 mg).

$^1$H-NMR (DMSO-d$_6$): δ(ppm) 0.47–0.56 (6H, m), 0.85 (9H, t, J=8.2), 2.38 (3H, s), 2.65–2.79 (2H, m), 2.86–2.98 (2H, m), 2.94 (3H, s), 4.00–4.06 (2H, m), 4.76–4.80 (1H, m), 6.65 (1H, dd, J=2.2, 8.5), 6.83 (1H, d, J=2.2), 7.03–7.15 (2H, m), 7.25–7.35 (4H, m), 7.39 (1H, d, J=8.5), 7.49 (2H, t, J=7.7), 7.60–7.64 (2H, m), 9.74 (1H, brs), 10.95 (1H, brs).

(Step E) Synthesis of (R)-N-[3-[2-[2-(3-methyl-2-phenyl-1H-indol-6-yloxy)ethylamino]-1-hydroxyethyl]phenyl] methanesulfonamide hydrochloride The compound (110 mg; obtained in the above step D) was dissolved in THF (1 mL), to which tetra-n-butylammonium fluoride (370 μL, 1 M THF solution) and acetic acid (21 μL) were added. After stirring at room temperature for 4 hours, the reaction mixture was purified by PTLC (4:1 chloroform/methanol). The thus obtained crude product was dissolved in ether. Ethanolic 0.5 N hydrochloric acid was added, followed by stirring. The generated precipitate was collected by filtration and dried to yield the title compound (33.9 mg).

$^1$H-NMR (DMSO-d$_6$): δ(ppm) 2.39 (3H, s), 3.00 (3H, s), 3.02–3.16 (2H, m), 3.22–3.34 (2H, m), 4.30–4.36 (2H, m), 4.96–5.04 (1H, m), 6.25 (1H, brs), 6.75 (1H, dd, J=2.2, 8.5), 6.91 (1H, d, J=2.2), 7.11–7.18 (2H, m), 7.30–7.53 (6H, m), 7.61–7.67 (2H, m), 8.90 (1H, brs), 9.09 (1H, brs), 9.85 (1H, s), 11.06 (1H, brs).

EXAMPLE 14

Synthesis of (R)-N-[3-[2-[2-(2,3-diphenyl-1H-indol-6-yloxy)ethylamino]-1-hydroxyethyl]phenyl] methanesulfonamide hydrochloride (Step A) Synthesis of 6-(2-aminoethoxy)-2,3-diphenyl-1H-indole 6-Hydroxy-2,3-diphenyl-1H-indole (2.50 g; synthesized according to the process described in *J. Chem. Soc.*, p. 5097 (1957)) was dissolved in N,N-dimethylacetamide (20 mL), to which N-benzyloxycarbonyl-2-bromoethylamine (2.93 g; synthesized according to the process described in WO 97/25311) and potassium carbonate (2.42 g) were added. After stirring at 70° C. for 14.5 hours, the reaction mixture was diluted with water and extracted with ethyl acetate. The organic layer was washed with saturated brine and then dried. The solvent was distilled off under reduced pressure. The residue was purified twice by silica gel column chromatography (9:1–1:1 hexane/ethyl acetate) to yield a compound (900 mg) as a brown amorphous solid. This was dissolved in a solution of 30% hydrobromic acid in acetic acid (10 mL), followed by stirring at room temperature for 1 hour. Ether (100 mL) was added to the reaction mixture and the generated precipitate was filtered. The compound obtained by filtration was dissolved in ethyl acetate. The thus obtained solution was washed with a saturated aqueous sodium bicarbonate solution and saturated brine and then dried. The solvent was distilled off under reduced pressure to yield the title compound (630 mg).

$^1$H-NMR (DMSO-d$_6$): δ(ppm) 1.99 (2H, brs), 2.92 (2H, t, J=5.8), 3.96 (2H, t, J=5.8), 6.72 (1H, dd, J=2.2, 8.5), 6.92 (1H, d, J=2.2), 7.24–7.43 (11H, m), 11.36 (1H, brs).

(Step B) Synthesis of (R)-N-[3-[2-[2-(2,3-diphenyl-1H-indol-6-yloxy)ethylamino]-1-triethylsilyloxyethyl]phenyl]methanesulfonamide The compound (328 mg; obtained in the above step A) was dissolved in N,N-dimethylacetamide (3.5 mL), to which (R)-N-[3-(2-iodo-1-triethylsilyloxyethyl)phenyl]methanesulfonamide (592 mg; synthesized according to the process described in WO 97/25311) and diisopropylethylamine (504 mg) were added. After stirring at 70° C. for 14.5 hours, the reaction mixture was diluted with water and extracted with ethyl acetate. The organic layer was washed with saturated brine and then dried. The solvent was distilled off under reduced pressure. The residue was purified by silica gel column chromatography (100:0–99:1 chloroform/methanol) to yield the title compound (257.8 mg).

$^1$H-NMR (DMSO-$d_6$): δ(ppm) 0.47–0.56 (6H, m), 0.85 (9H, t, J=7.7), 2.66–2.81 (2H, m), 2.86–2.98 (2H, m), 2.94 (3H, s), 4.02–4.10 (2H, m), 4.76–4.81 (1H, m), 6.69 (1H, dd, J=1.9, 7.9), 6.91 (1H, d, J=1.9), 7.10 (2H, dd, J=1.9, 7.9), 7.24–7.44 (14H, m), 9.70 (1H, brs), 11.35 (1H, brs).

(Step C) Synthesis of (R)-N-[3-[2-[2-(2,3-diphenyl-1H-indol-6-yloxy)ethylamino]-1-hydroxyethyl]phenyl]methanesulfonamide hydrochloride The compound (218 mg; obtained in the above step B) was dissolved in THF (2 mL), to which tetra-n-butylammonium fluoride (665 μL, 1 M THF solution) and acetic acid (38 μL) were added. After stirring at room temperature for 105 minutes, the reaction mixture was purified by PTLC (Preparative TLC; mfd. by Merck) (5:1 chloroform/10% concentrated ammonia water-containing methanol). The thus obtained crude product was dissolved in ether, to which ethanolic 0.1 N hydrochloric acid (3.0 mL) was added. After stirring, the solvent was distilled off under reduced pressure. Ether was added to the residue, followed by stirring. The generated precipitate was collected by filtration and dried to yield the title compound (125 mg).

$^1$H-NMR (DMSO-$d_6$): δ(ppm) 3.00 (3H, s), 3.04–3.54 (4H, m), 4.32–4.38 (2H, m), 4.99–5.06 (1H, m), 6.27 (1H, brs), 6.79 (1H, dd, J=2.2, 8.5), 7.00 (1H, d, J=2.2), 7.12–7.18 (2H, m), 7.26–7.46 (13H, m), 8.97 (1H, brs), 9.20 (1H, brs), 9.86 (1H, s), 11.49 (1H, brs).

EXAMPLE 15

Synthesis of (R)-N-[3-[2-[2-(2-tert-butyl-3-methyl-1H-indol-6-yloxy)ethylamino]-1-hydroxyethyl]phenyl]methanesulfonamide hydrochloride (Step A) Synthesis of 2-tert-butyl-6-methoxy-3-methyl-1H-indole 2-Bromo-5-methoxyaniline (1.01 g; synthesized according to the process reported by J. H. Tidwell et al., *J. Am. Chem. Soc.*, vol. 116, pp. 11797–11810 (1994)), 2,2-dimethyl-3-pentyne (480 mg; mfd. by Chemsampco), palladium acetate (28.1 mg), tetra-n-butylammonium chloride (1.39 g; mfd. by TOKYO KASEI), potassium carbonate (3.45 g) and triphenylphosphine (65.6 mg) were dissolved in N,N-dimethylacetamide (50 mL). After stirring at 100° C. for 20 hours, the reaction mixture was diluted with water and extracted with ether. The organic layer was washed with a saturated aqueous ammonium chloride solution and water, and then dried. The solvent was distilled off under reduced pressure. The residue was purified twice by silica gel column chromatography (5:1 hexane/ethyl acetate) to yield the title compound (202 mg).

$^1$H-NMR (CDCl$_3$): δ(ppm) 1.38 (9H, s), 2.27 (3H, s), 3.72 (3H, s), 6.57 (1H, dd, J=2.2, 8.5), 6.78 (1H, d, J=2.2), 7.23 (1H, d, J=8.5), 10.19 (1H, brs).

(Step B) Synthesis of 2-tert-butyl-6-hydroxy-3-methyl-1H-indole

The compound (200 mg; obtained in the above step A) was dissolved in dehydrated methylene chloride (5 mL), followed by stirring under an argon atmosphere at 0° C. A solution of 1 N boron tribromide in methylene chloride (5 mL) was added dropwise. The resulting mixture was stirred for 2 hours while the temperature was gradually cooled down to room temperature. The reaction mixture was cooled with ice. Water (10 mL) was added dropwise with vigorous stirring. The organic layer was separated and the aqueous layer was extracted with ethyl acetate. The combined organic layers were washed with saturated brine and then dried over anhydrous sodium sulfate. The solvent was distilled off under reduced pressure. The residue was purified by silica gel column chromatography (5:1–4:1 hexane/ethyl acetate) to yield the title compound (170 mg).

$^1$H-NMR (CDCl$_3$): δ(ppm) 1.43 (9H, s), 2.35 (3H, s), 4.62 (1H, brs), 6.63 (1H, dd, J=2.2, 8.5), 6.75 (1H, d, J=2.2), 7.31 (1H, d, J=8.5), 7.67 (1H, brs).

(Step C) Synthesis of (R)-2-[N'-benzyl-N'-[2-(2-tert-butyl-3-methyl-1H-indol-6-yloxy)ethyl]amino]-1-[3-(N-benzyl-N-methylsulfonylamino)phenyl]ethanol (R)-2-[N'-Benzyl-N'-(2-hydroxyethyl)amino]-1-[3-(N-benzyl-N-methylsulfonylamino)phenyl]ethanol (173 mg; synthesized according to the process described in WO 01/04092) and triphenylphosphine (103 mg) were dissolved in dehydrated methylene chloride (5 mL), followed by stirring at −20° C. N-Bromosuccinimide (69.9 mg) was added at a stretch and the resulting mixture was stirred for 10 minutes. The reaction mixture was purified by silica gel column chromatography (5:1–3:1 hexane/ethyl acetate) to yield (R)-2-[N'-benzyl-N'-(2-bromoethyl)amino]-1-[3-(N-benzyl-N-methylsulfonylamino)phenyl]ethanol. This was immediately dissolved in acetonitrile (2.5 mL). The compound (79.8 mg; obtained in the above step B) and an aqueous 1 N sodium hydroxide solution (392 μL) were added, followed by stirring at room temperature for 14 hours. The reaction mixture was concentrated and the residue was purified by silica gel column chromatography (4:1–2:1 hexane/ethyl acetate) to yield the title compound (132.2 mg).

$^1$H-NMR (CDCl$_3$): δ(ppm) 1.43 (9H, s), 2.36 (3H, s), 2.55–2.84 (2H, m), 2.86 (3H, s), 2.90–3.14 (2H, m), 3.67 (1H, d, J=13.5), 3.93 (1H, d, J=13.5), 4.06 (2H, t, J=6.0), 4.65 (1H, dd, J=3.3, 10.1), 4.77 (2H, s), 6.75 (1H, dd, J=2.2, 8.5), 6.82 (1H, d, J=2.2), 7.07–7.37 (15H, m), 7.87 (1H, brs).

(Step D) Synthesis of (R)-N-[3-[2-[2-(2-tert-butyl-3-methyl-1H-indol-6-yloxy)ethylamino]-1-hydroxyethyl]phenyl]methanesulfonamide hydrochloride The compound (100 mg; obtained in the above step C) was dissolved in a mixed solvent of THF (1 mL) and methanol (1 mL), to which 20% palladium hydroxide/carbon powder (40 mg, 50% moisture) was added. The atmosphere in the system was replaced with hydrogen, followed by stirring at room temperature for 20 hours. The reaction mixture was filtered and the filtrate was placed under reduced pressure to distill the solvent off. To the residue, ethanolic 0.1 N hydrochloric acid (16 mL) was added. After stirring at room temperature for 10 minutes, the solvent was distilled off. Ether was added to the residue. The deposited crystal was collected by filtration and dried to yield the title compound (76.6 mg).

$^1$H-NMR (DMSO-$d_6$): δ(ppm) 1.39 (9H, s), 2.28 (3H, s), 3.00 (3H, s), 3.00–3.30 (2H, m), 3.40–3.50 (2H, m), 4.25–4.29 (2H, m), 4.98–5.11 (1H, m), 6.20 (1H, brs), 6.66 (1H, dd, J=2.2, 8.5), 6.84 (1H, d, J=2.2), 7.11–7.18 (2H, m), 7.26–7.38 (3H, m), 8.91 (1H, brs), 9.15 (1H, brs), 9.85 (1H, brs), 10.29 (1H, brs).

EXAMPLE 16

Synthesis of (R)-N-[3-[2-[2-(2-methyl-3-phenyl-1H-indol-6-yloxy)ethylamino]-1-hydroxyethyl]phenyl]methanesulfonamide hydrochloride (Step A) Synthesis of 3-bromo-2-methoxycarbonyl-6-methoxy-1H-indole 2-Methoxycarbonyl-6-methoxy-1H-indole (1.00 g; mfd. by Aldrich) was dissolved in DMF (51.2 mL) under an argon atmosphere, followed by stirring at 0° C. A solution of N-bromosuccinimide (1.02 g) in DMF (21.7 mL) was added dropwise over 30 minutes. The reaction mixture was maintained at 0° C. and stirred for 2.5 hours. The reaction mixture was poured into an ice water. After stirring, the resulting mixture was extracted with ethyl acetate. The organic layer was washed with a saturated aqueous sodium bicarbonate solution and saturated brine, and then dried. The solvent was distilled off under reduced pressure. The residue was purified by silica gel column chromatography (4:1–3:1 hexane/ethyl acetate) to yield the title compound (760 mg).

$^1$H-NMR (CDCl$_3$): δ(ppm) 3.86 (3H, s), 3.97 (3H, s), 6.79 (1H, d, J=2.2), 6.89 (1H, dd, J=2.2, 8.8), 7.53 (1H, d, J=8.8), 8.87 (1H, brs).

(Step B) Synthesis of 2-methoxycarbonyl-6-methoxy-3-phenyl-1H-indole

The compound (700 mg; obtained in the above step A) was dissolved in toluene (10 mL). Phenylboric acid (1.43 g; mfd. by Aldrich), potassium carbonate (649 mg) and tetrakis(triphenylphosphine)palladium(0) (271.3 mg; mfd. by Nacalai Tesque) were added and the resulting mixture was heated to reflux for 5 hours. The reaction mixture was diluted with ethyl acetate and was quenched with a mixture of 30% hydrogen peroxide solution (5 mL) and water (100 mL). The organic layer was washed with a saturated aqueous sodium bicarbonate solution and saturated brine, and then dried. The solvent was distilled off under reduced pressure. The residue was purified by silica gel column chromatography (5:1–2:1 hexane/ethyl acetate) to yield the title compound (560 mg).

$^1$H-NMR (CDCl$_3$): δ(ppm) 3.80 (3H, s), 3.88 (3H, s), 6.81 (1H, dd, J=2.2, 8.5), 6.85 (1H, d, J=2.2), 7.35–7.57 (6H, m), 8.82 (1H, brs).

(Step C) Synthesis of 2-hydroxymethyl-6-methoxy-3-phenyl-1H-indole

The compound (560 mg; obtained in the above step B) was dissolved in dehydrated THF (20 mL). Lithium aluminium hydride (151 mg) was added and the resulting mixture was stirred at 40° C. for 90 minutes. After gradually adding an aqueous 1 N sodium hydroxide solution, the reaction mixture was extracted with ethyl acetate. The organic layer was washed with saturated brine. The solvent was distilled off under reduced pressure to yield the title compound (1.40 g).

$^1$H-NMR (CDCl$_3$): δ(ppm) 1.90 (1H, t, J=5.8), 3.86 (3H, s), 4.88 (2H, d, J=5.8), 6.81 (1H, dd, J=2.2, 8.5), 6.87 (1H, d, J=2.2), 7.29–7.36 (1H, m), 7.42–7.48 (4H, m), 7.58 (1H, d, J=8.5), 8.40 (1H, brs).

(Step D) Synthesis of 2-methyl-6-methoxy-3-phenyl-1H-indole

The compound (253.3 mg; obtained in the above step C) was dissolved in dehydrated dioxane (12 mL). After adding lithium aluminium hydride (379 mg), the resulting mixture was stirred at 100° C. for 47 hours. The reaction mixture was allowed to cool down to room temperature, and then gradually added dropwise to ice water. An aqueous 5 N sodium hydroxide solution (100 mL) was added, followed by extraction with ether. The organic layer was washed with saturated brine and then dried. The solvent was distilled off under reduced pressure. The residue was purified by silica gel column chromatography (5:1–1:1 hexane/ethyl acetate) to yield the title compound (146 mg).

$^1$H-NMR (CDCl$_3$): δ(ppm) 2.48 (3H, s), 3.86 (3H, s), 6.78 (1H, dd, J=2.2, 8.5), 6.85 (1H, d, J=2.2), 7.26–7.32 (1H, m), 7.42–7.55 (5H, m), 7.81 (1H, brs).

(Step E) Synthesis of 6-hydroxy-2-methyl-3-phenyl-1H-indole

The compound (146 mg; obtained in the above step D) was dissolved in dehydrated methylene chloride (5 mL) under an argon atmosphere, followed by stirring at 0° C. A solution of 1 M boron tribromide in methylene chloride (2 mL) was added. The resulting mixture was stirred for 3.5 hours while the temperature was gradually allowed to cool down to room temperature. The reaction mixture was cooled with ice and water (20 mL) was gradually added dropwise. The mixture was extracted with ethyl acetate. The organic layer was washed with saturated brine, and then dried. The solvent was distilled off under reduced pressure. The residue was purified by silica gel column chromatography (5:1–3:1 hexane/ethyl acetate) to yield the title compound (116 mg).

$^1$H-NMR (CDCl$_3$): δ(ppm) 2.46 (3H, s), 4.77 (1H, brs), 6.66 (1H, dd, J=2.2, 8.5), 6.79 (1H, d, J=2.2), 7.24–7.32 (1H, m), 7.41–7.51 (5H, m), 7.81 (1H, brs).

(Step F) Synthesis of (R)-2-[N'-benzyl-N'-[2-(2-methyl-3-phenyl-1H-indol-6-yloxy)ethyl]amino]-1-[3-(N-benzyl-N-methylsulfonylamino)phenyl]ethanol (R)-2-[N'-Benzyl-N'-(2-hydroxyethyl)amino]-1-[3-(N-benzyl-N-methylsulfonylamino)phenyl]ethanol (273 mg; synthesized according to the process described in WO 01/04092) and triphenylphosphine (162 mg) were dissolved in dehydrated methylene chloride (8 mL) under an argon atmosphere, followed by stirring at −20° C. After adding N-bromosuccinimide (110 mg) at a stretch, the resulting mixture was stirred for 10 minutes. The reaction mixture was purified by silica gel column chromatography (5:1–3:1 hexane/ ethyl acetate) to yield (R)-2-[N'-benzyl-N'-(2-bromoethyl)amino])-1-[3-(N-benzyl-N-methylsulfonylamino)phenyl]ethanol. This was immediately dissolved in acetonitrile (4 mL), to which the compound (116 mg; obtained in the above step E) and an aqueous 1 N sodium hydroxide solution (521 μL) were added. The resulting mixture was stirred at room temperature for 16 hours and the reaction mixture was then concentrated. The residue was purified by silica gel column chromatography (5:1–1:1 hexane/ethyl acetate) to yield the title compound (243 mg).

$^1$H-NMR (CDCl$_3$): δ(ppm) 2.44 (3H, s), 2.55–2.63 (1H, m), 2.77–2.83 (1H, m), 2.87 (3H, s), 2.91–2.99 (1H, m), 3.04–3.12 (1H, m), 3.67 (1H, d, J=13.7), 3.93 (1H, d, J=13.7), 4.06 (2H, d, J=6.3), 4.65 (1H, dd, J=3.3, 9.9), 4.77 (2H, s), 6.77 (1H, dd, J=2.2, 8.5), 6.85 (1H, d, J=2.2), 7.08–7.12 (1H, m), 7.16–7.34 (15H, m), 7.41–7.54 (4H, m), 8.10 (1H, brs).

(Step G) Synthesis of (R)-N-[3-[2-[2-(2-methyl-3-phenyl-1H-indol-6-yloxy)ethylamino]-1-hydroxyethyl]phenyl]methanesulfonamide hydrochloride The compound (135 mg; obtained in the above step F) was dissolved in a mixed solvent of THF (2 mL) and methanol (2 mL), to which 20% palladium hydroxide/carbon powder (67.5 mg; 50% moisture) was added. The atmosphere in the system was replaced with hydrogen, followed by stirring at room temperature for 19 hours. The reaction mixture was filtered and the filtrate was placed under reduced pressure to distill the solvent off. To the residue, ethanolic 0.1 N hydrochloric acid (20.4 mL) was added. After stirring at room temperature for 10 minutes, the solvent was distilled off. Ether was added to the residue. The deposited crystal was collected by filtration and dried to yield the title compound (69.1 mg).

$^1$H-NMR (DMSO-$d_6$): δ(ppm) 2.44 (3H, s), 3.00 (3H, s), 3.00–3.48 (4H, m), 4.27–4.34 (2H, m), 4.95–5.02 (1H, m), 6.26 (1H, brs), 6.74 (1H, dd, J=2.2, 8.5), 6.91 (1H, d, J=2.2), 7.12–7.17 (2H, m), 7.23–7.47 (7H, m), 8.88 (1H, brs), 9.03 (1H, brs), 9.85 (1H, brs), 11.06 (1H, brs).

EXAMPLE 17

Synthesis of (R)-N-[5-[2-[2-(3-methyl-2-phenyl-1H-indol-6-yloxy)ethylamino]-1-hydroxyethyl]-2-chlorophenyl]methanesulfonamide hydrochloride (Step A) Synthesis of (R)-N-[5-[2-[2-(3-methyl-2-phenyl-1H-indol-6-yloxy)ethylamino]-1-triethylsilyloxyethyl]-2-chlorophenyl]methanesulfonamide The compound (266 mg; obtained in the step C of Example 13) was dissolved in acetonitrile (5 mL). After adding (R)-N-[5-(2-iodo-1-triethylsilyloxyethyl)-2-chlorophenyl]methanesulfonamide (490 mg; synthesized according to the process described in WO 97/25311) and diisopropylethylamine (646 mg), the resulting mixture was stirred at 80° C. for 16.5 hours. The reaction mixture was diluted with water and then extracted with ethyl acetate. The organic layer was washed with water and saturated brine, and then dried. The solvent was distilled off under reduced pressure. The residue was purified by silica gel column chromatography (99:1 chloroform/methanol) to yield the title compound (99 mg).

$^1$H-NMR (CDCl$_3$): δ(ppm) 0.52–0.60 (6H, m), 0.89 (9H, t, J=7.9), 2.43 (3H, s), 2.75–2.91 (2H, m), 2.95 (3H, s), 3.01 (2H, t, J=5.2), 4.10 (2H, t, J=5.2), 4.83 (1H, m), 6.77 (1H, dd, J=2.2, 8.5), 6.86 (1H, d, J=2.2), 7.15 (1H, dd, J=2.2, 8.5), 7.29–7.38 (2H, m), 7.43–7.58 (5H, m), 7.67 (1H, d, J=2.2), 8.05 (1H, brs).

(Step B) Synthesis of (R)-N-[5-[2-[2-(3-methyl-2-phenyl-1H-indol-6-yloxy)ethylamino]-1-hydroxyethyl]-2-chlorophenyl]methanesulfonamide hydrochloride The compound (99 mg; obtained in the above step A) was reacted according to the procedure of the step E of Example 13 to yield the title compound (50 mg).

$^1$H-NMR (DMSO-$d_6$): δ(ppm) 2.39 (3H, s), 3.06 (3H, s), 3.04–3.52 (4H, m), 4.29–4.36 (2H, m), 5.00–5.08 (1H, m), 6.36 (1H, m), 6.75 (1H, dd, J=2.2, 8.5), 6.91 (1H, d, J=2.2), 7.28–7.36 (2H, m), 7.43–7.65 (7H, m), 8.96 (1H, brs), 9.03 (1H, brs), 9.55 (1H, s), 11.05 (1H, s).

EXAMPLE 18

Synthesis of (R)-N-[3-[2-[2-(2,3-dimethylbenzofuran-6-yloxy)ethylamino]-1-hydroxyethyl]phenyl]methanesulfonamide hydrochloride (Step A) Synthesis of 6-[2-(N-benzyloxycarbonyl)aminoethoxy]-2,3-dimethylbenzofuran 6-Hydroxy-2,3-dimethylbenzofuran (324 mg; synthesized according to the process described in *J. Heterocyclic Chem.*, vol. 36, p. 509 (1999)), N-benzyloxycarbonyl-2-bromoethylamine (516 mg; synthesized according to the process described in WO 97/25311) and potassium carbonate (691 mg) were reacted according to the procedure of the step B of Example 13 to yield the title compound (398 mg).

$^1$H-NMR (CDCl$_3$): δ(ppm) 2.10 (3H, s), 2.33 (3H, s), 3.59 (2H, quartet, J=5.2), 4.03 (2H, t, J=4.9), 5.10 (2H, s), 5.29 (1H, brs), 6.78 (1H, dd, J=2.2, 8.2), 6.88 (1H, d, J=2.2), 7.23 (1H, d, J=8.2), 7.24–7.36 (5H, m).

(Step B) Synthesis of 6-(2-aminoethoxy)-2,3-dimethylbenzofuran hydrobromide

The compound (393 mg; obtained in the above step A) was dissolved in a solution of 30% hydrobromic acid in acetic acid (5 mL), followed by stirring at room temperature for 2.5 hours. Ether was added to the reaction mixture. The generated precipitate was collected by filtration, washed with ether and dried to yield the title compound (255 mg).

$^1$H-NMR (DMSO-$d_6$): δ(ppm) 2.10 (3H, s), 2.33 (3H, s), 3.20–3.30 (2H, m), 4.17 (2H, t, J=4.9), 6.89 (1H, dd, J=2.2, 8.5), 7.13 (1H, d, J=2.2), 7.37 (1H, d, J=8.5), 7.97 (3H, brs).

(Step C) Synthesis of (R)-N-[3-[2-[2-(2,3-dimethylbenzofuran-6-yloxy)ethylamino]-1-triethylsilyloxyethyl]phenyl]methanesulfonamide The compound (143 mg; obtained in the above step B), (R)-N-[3-(2-iodo-1-triethylsilyloxyethyl)phenyl]methanesulfonamide (227 mg; synthesized according to the process described in WO 97/25311) and diisopropylethylamine (323 mg) were reacted according to the procedure of the step D of Example 13 to yield the title compound (38.9 mg).

$^1$H-NMR (CDCl$_3$): δ(ppm) 0.50–0.61 (6H, m), 0.88 (9H, t, J=7.9), 2.11 (3H, s), 2.34 (3H, s), 2.74–3.06 (4H, m), 2.96 (3H, s), 4.08 (2H, t, J=5.2), 4.81–4.86 (1H, m), 6.79 (1H, dd, J=2.2, 8.5), 6.90 (1H, d, J=2.2), 7.13–7.34 (5H, m).

(Step D) Synthesis of (R)-N-[3-[2-[2-(2,3-dimethylbenzofuran-6-yloxy)ethylamino]-1-hydroxyethyl]phenyl]methanesulfonamide hydrochloride The compound (38.9 mg; obtained in the above step C) was reacted according to the procedure of the-step E of Example 13 to yield the title compound (14.8 mg).

$^1$H-NMR (DMSO-$d_6$): δ(ppm) 2.10 (3H, s), 2.34 (3H, s), 3.00 (3H, s), 3.00–3.46 (4H, m), 4.28–4.34 (2H, m), 4.92–4.99 (1H, m), 6.20–6.24 (1H, m), 6.89 (1H, dd, J=2.2, 8.5), 7.11–7.17 (3H, m), 7.29–7.39 (3H, m), 8.87 (2H, brs), 9.84 (1H, s).

EXAMPLE 19

Synthesis of (R)-N-[3-[2-[2-(2,3-dimethylbenzothiophen-6-yloxy)ethylamino]-1-hydroxyethyl]phenyl]methanesulfonamide hydrochloride (Step A) Synthesis of 6-[2-(N-benzyloxycarbonyl)aminoethoxy]-2,3-dimethylbenzothiophene 6-Hydroxy-2,3-dimethylbenzothiophene (356 mg; synthesized according to the process described in *Phosphorus, Sulfur and Silicon*, vol. 153–154, p. 397 (1999)), N-benzyloxycarbonyl-2-bromoethylamine (516 mg; synthesized according to the process described in WO 97/25311) and potassium carbonate (691 mg) were reacted according to the procedure of the step B of Example 13 to yield the title compound (356 mg).

$^1$H-NMR (CDCl$_3$): δ(ppm) 2.25 (3H, s), 2.43 (3H, s), 3.62 (2H, quartet, J=5.2), 4.07 (2H, t, J=4.9), 5.11 (2H, s), 5.26 (1H, brs), 6.93 (1H, dd, J=2.2, 8.5), 7.20 (1H, d, J=2.2), 7.28–7.38 (5H, m), 7.44 (1H, d, J=8.5).

(Step B) Synthesis of 6-(2-aminoethoxy)-2,3-dimethylbenzothiophene hydrobromide

The compound (356 mg; obtained in the above step A) was reacted according to the procedure of the step B of Example 18 to yield the title compound (237 mg).

$^1$H-NMR (DMSO-$d_6$): δ(ppm) 2.23 (3H, s), 2.41 (3H, s), 3.20–3.30 (2H, m), 4.21 (2H, t, J=4.9), 7.03 (1H, dd, J=2.5, 8.8), 7.50 (1H, d, J=2.5), 7.57 (1H, d, J=8.8), 7.97 (3H, brs).

(Step C) Synthesis of (R)-N-[3-[2-[2-(2,3-dimethylbenzothiophen-6-yloxy)ethylamino]-1-triethylsilyloxyethyl]phenyl]methanesulfonamide The compound (151 mg; obtained in the above step B), (R)-N-[3-(2-iodo-1-triethylsilyloxyethyl)phenyl] methanesulfonamide (227 mg; synthesized according to the process described in WO 97/25311) and diisopropylethylamine (323 mg) were reacted according to the procedure of the step D of Example 13 to yield the title compound (41.6 mg).

$^1$H-NMR (CDCl$_3$): δ(ppm) 0.50–0.59 (6H, m), 0.88 (9H, t, J=7.7), 2.25 (3H, s), 2.43 (3H, s), 2.74–3.05 (4H, m), 3.01 (3H, s), 4.10 (2H, t, J=5.2), 4.81–4.85 (1H, m), 6.92 (1H, dd, J=2.2, 8.5), 7.13–7.34 (5H, m), 7.44 (1H, d, J=8.5).

(Step D) Synthesis of (R)-N-[3-[2-[2-(2,3-dimethylbenzothiophen-6-yloxy)ethylamino]-1-hydroxyethyl]phenyl]methanesulfonamide hydrochloride The compound (41.6 mg; obtained in the above step C) was reacted according to the procedure of the step E of Example 13 to yield the title compound (15.6 mg).

$^1$H-NMR (DMSO-d$_6$): δ(ppm) 2.24 (3H, s), 2.41 (3H, s), 2.96–3.48 (4H, m), 3.00 (3H, s), 4.32–4.38 (2H, m), 4.92–5.00 (1H, m), 6.21–6.26 (1H, m), 7.03 (1H, dd, J=2.2, 8.5), 7.11–7.17 (2H, m), 7.29–7.31 (1H, m), 7.35 (1H, t, J=7.7), 7.51 (1H, d, J=2.2), 7.57 (1H, d, J=8.8), 8.90 (2H, brs), 9.84 (1H, brs).

Further, the other compounds listed in Table 2 can be also prepared by repeating the procedures described in the present specification using the intermediates described in WO 97/25311 and WO 01/04092.

TABLE 2

(I)

| Example No. | R$^1$ | R$^2$ | Y | X | R$^5$ | R$^6$ |
|---|---|---|---|---|---|---|
| 20 | Cl | NHSO$_2$CH$_3$ | O | NH | CH$_3$ | Ph |
| 21 | Cl | NHSO$_2$CH$_3$ | O | NH | CH$_3$ | tBu |
| 22 | Cl | NHSO$_2$CH$_3$ | O | NH | Ph | CH$_3$ |
| 23 | Cl | NHSO$_2$CH$_3$ | O | O | CH$_3$ | CH$_3$ |
| 24 | Cl | NHSO$_2$CH$_3$ | O | S | CH$_3$ | CH$_3$ |
| 25 | F | NHSO$_2$CH$_3$ | O | NH | CH$_3$ | CH$_3$ |
| 26 | F | NHSO$_2$CH$_3$ | O | NH | CH$_3$ | Ph |
| 27 | F | NHSO$_2$CH$_3$ | O | NH | Ph | CH$_3$ |
| 28 | F | NHSO$_2$CH$_3$ | O | O | CH$_3$ | CH$_3$ |
| 29 | F | NHSO$_2$CH$_3$ | O | S | CH$_3$ | CH$_3$ |
| 30 | OH | SO$_2$NHCH$_3$ | O | NH | CH$_3$ | Ph |
| 31 | OH | SO$_2$NHCH$_3$ | O | NH | Ph | CH$_3$ |
| 32 | OH | SO$_2$NHCH$_3$ | O | O | CH$_3$ | CH$_3$ |
| 33 | OH | SO$_2$NHCH$_3$ | O | S | CH$_3$ | CH$_3$ |
| 34 | H | NHSO$_2$CH$_3$ | O | NH | CH$_3$ | 4-OMe—Ph |
| 35 | H | NHSO$_2$CH$_3$ | O | NH | CH$_3$ | 3-OMe—Ph |
| 36 | H | NHSO$_2$CH$_3$ | O | NH | CH$_2$CH$_3$ | 4-OMe—Ph |
| 37 | H | NHSO$_2$CH$_3$ | O | NH | CH$_3$ | 4-OH—Ph |
| 38 | H | NHSO$_2$CH$_3$ | O | NH | CH$_3$ | 3-OH—Ph |
| 39 | H | NHSO$_2$CH$_3$ | O | NH | CH$_2$CH$_3$ | 4-OH—Ph |

TEST EXAMPLE 1

Human β3-Agonist Activities

Human β3-agonist activities were determined using CHO (Chinese hamster ovary) cells transfected with pcDNA3 (mfd. by Invitrogen) to which human β3 gene had been inserted. Human β3 fragment was first obtained from human adipose tissue cDNA (mfd. by Clonetech) by PCR using the primer of β3 (Krief, et al., *J. Clin. Invest.*, vol. 91, pp. 344–349 (1993)). The human β3 fragment thus obtained was used as a probe to obtain the full length human β3 gene from a human genomic library (mfd. by Clonetech). The above cells were cultured in a Ham F-12 medium supplemented with 10% fetal bovine serum, 400 μg/mL geneticin (Gibco BRL), 100 U/mL penicillin and 100 μg/mL streptomycin. After placing these cells (5×10$^5$) into a 6-well plate and culturing them for 24 hours, they were allowed to stand on a serum-free Ham F-12 medium for 2 hours. The compound was first dissolved in DMSO, diluted to a concentration of 10$^{-6}$ M with Ham F-12 supplemented with 1 mM isobutylmethylxanthine and 1 mM ascorbic acid, and then added to the cells. After the cells were cultured for 30 minutes, the medium was removed, followed by addition of 0.5 mL of 1 N NaOH. The medium was allowed to stand for 20 minutes and then 0.5 mL of 1 N acetic acid was added to the medium. The medium was stirred and centrifuged, followed by quantitating cAMP with cAMP EIA kit (mfd. by Cayman). With respect to eight compounds among the compounds described in Examples, their relative activities (%) as compared with isoproterenol were indicated in Table 3. Isoproterenol was purchased from RBI (Research Biochemicals International). The results from Table 3 indicate that the compounds of the present invention have human β3-agonist activities.

TEST EXAMPLE 2

Action on the Heart

The heart was excised from a male guinea pig weighing 180–250 g to prepare a specimen of the right atrium. The specimen was set in an organ bath filled with a Krebs solution which had been aerated with a mixed gas of 5% CO$_2$/95% O$_2$. The automaticity was determined using a isometric transducer (NIHON KOHDEN TB-611T) connected to a polygraph (NIHON KOHDEN MR-6000). At a concentration of 10$^{-6}$ M, the present compounds described in Examples had no actions on the automaticity of the right atrium specimen. Therefore, these compounds were expected to have selective actions and hardly induce an increase of the heart rate, that is, to entail few side effects.

TEST EXAMPLE 3

Pharmacological Effect on a Transgenic Mouse Expressing Human β3

Since β3 is species-specific (Strosberg, et al., *Trends Pharmacol. Sci.*, vol. 17, pp. 373–381 (1996); Strosberg, et al., *Annu. Rev. Pharmacol. Toxicol.*, vol. 37, pp. 421–450 (1997)), pharmacological tests using a transgenic mouse expressing human β3 are more effective than those using a normal mouse or rat. Ito, et al. prepared a replacement mouse expressing human β3 in its brown fat by introducing human β3 gene into a mouse whose mouse β3 gene had been knocked out (Ito, et al., *Diabetes*, vol. 47, pp. 1464–1471 (1998)). A compound of the present invention can be tested for antiobestic activity and antidiabetic activity using a transgenic mouse according to the following procedures.

The lipolytic activity can be examined in vitro according to the method reported by Rodbell (*J. Biol. Chem.*, vol. 239, pp. 375–380 (1964)) wherein the method comprises gathering an epididymis white adipose tissue or the like from a transgenic mouse; preparing a suspension of the cell in Krebs-Ringer buffer solution containing 4% bovine serum albumin at the cell density of $2 \times 10^5$ cell/mL; putting 300 μL aliquots of the suspension into separate Eppendorf tubes; adding into separate tubes, 300 μL aliquots of a medium comprising dissolved therein a compound to be tested; maintaining the temperature at 37° C. for 1 hour while shaking; quenching the stimulation with ice cooling; removing adipocytes with an aspirator after centrifugation; and quantifying free glycerol with F-kit glycerol (Boehringer Mannheim).

The hypoglycemic effect can be examined as follows. After fasted for four hours, a transgenic mouse is orally dosed with a test compound dissolved in 10% hydroxypropyl-β-cyclodextrin (Aldrich) at a dose of 0.1 mL/10 g body weight. After 0 minute, 30 minutes, 1 hour and 2 hours, blood samples are collected from venous plexus of the eyeground.

The glucose tolerance can be examined as follows. After fasted overnight, a transgenic mouse is intraperitoneally dosed with glucose (Wako Pure Chemical Industries) at a dose of 1.5 g/kg and orally dosed with a test compound dissolved in 10% hydroxypropyl-β-cyclodextrin (Aldrich) at a dose of 0.1 mL/10 g body weight. After 0 minute, 30 minutes, 1 hour and 2 hours, blood samples are collected from venous plexus of the eyeground. A blood glucose level is determined by measuring the serum glucose concentration in the sample using Glucose Test B Test Wako (Wako Pure Chemical Industries). [Decrease of blood glucose(%)=(A−B)/(A−C)×100 wherein A represents the glucose concentration after the loading of glucose; B represents the glucose concentration after the administration of a medicinal substance; and C represents the glucose concentration at normal times] An insulin level is measured using Insulin Measurement Kit (EIA, Morinaga Bioscience Research Institute) with mouse insulin as the standard.

The lipolytic activity can be examined as follows. After fasted for four hours, a transgenic mouse is orally dosed with a test compound dissolved in 10% hydroxypropyl-β-cyclodextrin (Aldrich) at a dose of 0.1 mL/10 g body weight. After 0 minute, 30 minutes, 1 hour and 2 hours, blood samples are collected from venous plexus of the eyeground. A free fatty acid level in the serum obtained from the above sample is measured using NEFA HA Test Wako (Wako Pure Chemical Industries).

The thermogenesis can be measured with OXYMAX System (Columbus) according to the method reported by Largis et al. (*Drug Development Research*, vol. 32, pp. 69–76 (1994)). According to this device, the amount of thermogenesis can be obtained by calculating the calories based on the amount of oxygen consumed and the amount of carbon dioxide generated. After the administration of a medicinal substance, the measurements are carried out for 120 minutes (15 points). The average of the measured values obtained for the latter 90 minutes (10 points) is converted into a value per body weight to give the amount of thermogenesis. When a test by repetitive administrations is carried out, a medicinal substance may be administered at a dose once daily, twice daily or the like. The duration of administration may be 1 week, 2 weeks or more. In a test by repetitive administrations, body weight, blood glucose level and insulin level can be monitored with the passage of time as the method of Largis et al. (*Drug Development Research*, vol. 32, pp. 69–76 (1994). It is also possible that after the completion of the administration, the animal is anatomized to measure the weight of fat tissue or to prepare a section followed by a microscopic examination. Further, the expression level of UCP-1 can be examined according to the method reported by Nagase et al. (*J. Clin. Invest.*, vol. 97, pp. 2898–2904 (1996)).

The present compounds were orally administered to transgenic mice in an amount of from 3 to 10 mg/kg to measure their thermogenesis. The administration of the compound of Example 10, 11 or 13 resulted in increasing the thermogenesis by 15%, 17% or 15% respectively as compared with the control group. These results showed that the compounds of the present invention posses thermogenesis increasing activities.

TEST EXAMPLE 4

Toxicity Test

Each of the present compounds synthesized in Examples 3, 9 and 10 was orally administered to 6-week old male ddy mice (CHARLES RIVER JAPAN) at 100 mg/kg, and none of eight animals were found to be dead. The other compounds got the same results. Therefore, this test showed a low toxicity of the present compounds.

TABLE 3

| Compound | $EC_{50}$ (nM) | Intrinsic activity* (%) |
|---|---|---|
| Example 3 | 8.7 | 100 |
| Example 4 | 10 | 73 |
| Example 9 | 16 | 62 |
| Example 10 | 4.5 | 78 |
| Example 11 | 4.8 | 80 |
| Example 12 | 5.3 | 71 |
| Example 13 | 14 | 96 |
| Example 17 | 4.4 | 94 |

*Relative activities (%) as compared with isoproterenol.

All the publications, patents and patent applications cited in this specification are incorporated herein in their entities by reference.

Industrial Utility

Compounds of the present invention are novel compounds having a high human β3-adrenoreceptor stimulating activity. Therefore, compounds of the present invention are useful as a medicine for treating and preventing β3-adrenoreceptor associated diseases, such as diabetes, obesity, hyperlipidemia and urinary disturbances.

What is claimed is:

1. A compound of the general formula (II):

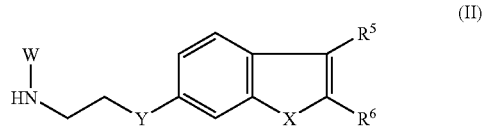

or a salt thereof,
wherein
W represents a hydrogen atom or an amino-protecting group;
$R^5$ and $R^6$ may be the same or different and each independently represents a hydrogen atom, an alkyl group containing from 1 to 6 carbon atoms, an optionally substituted phenyl group or an optionally substituted benzyl group, provided that $R^5$ and $R^6$ do not represent a hydrogen atom at the same time;
X represents NH;
Y represents an oxygen atom, $NR^7$, a sulfur atom, a methylene group or a bond; and R⁷ represents a hydrogen atom, an alkyl group containing from 1 to 6 carbon atoms, or an acyl group containing from 1 to 6 carbon atoms.

2. A compound of the general formula (II):

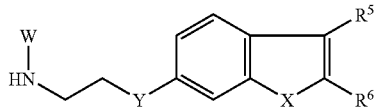

(II)

or a salt thereof,
wherein
W represents a hydrogen atom or an amino-protecting group;
R⁵ and R⁶ may be the same or different and each independently represents a hydrogen atom, an alkyl group containing from 1 to 6 carbon atoms, an optionally substituted phenyl group or an optionally substituted benzyl group, provided that R⁵ and R⁶ do not represent a hydrogen atom at the same time;
X represents NH;
Y represents an oxygen atom, NR⁷ or a sulfur atom; and
R⁷ represents a hydrogen atom, an alkyl group containing from 1 to 6 carbon atoms, or an acyl group containing from 1 to 6 carbon atoms.

3. The compound as claimed in claim 2, which is a compound selected from the group consisting of:

2-(2,3-dimethyl-1H-indol-6-yloxy)ethylcarbamic acid benzyl ester;

2-(2,3-dimethyl-1H-indol-6-yloxy)ethylamine;

N-benzyl-N-[2-(2,3-dimethyl-1H-indol-6-yloxy)ethyl]amine;

2-(3-methyl-2-phenyl-1H-indol-6-yloxy)ethylcarbamic acid benzyl ester;

2-(3-methyl-2-phenyl-1H-indol-6-yloxy)ethylamine;

N-benzyl-N-[2-(3-methyl-2-phenyl-1H-indol-6-yloxy)ethyl]amine;

2-(2-methyl-3-phenyl-1H-indol-6-yloxy)ethylcarbamic acid benzyl ester;

2-(2-methyl-3-phenyl-1H-indol-6-yloxy)ethylamine;

2-(2,3-dimethylbenzofuran-6-yloxy)ethylcarbamic acid benzyl ester;

2-(2,3-dimethylbenzofuran-6-yloxy)ethylamine;

N-benzyl-N-[2-(2,3-dimethylbenzofuran-6-yloxy)ethyl]amine;

2-(2,3-dimethylbenzothiophen-6-yloxy)ethylcarbamic acid benzyl ester;

2-(2,3-dimethylbenzothiophen-6-yloxy)ethylamine; and

N-benzyl-N-[2-(2,3-dimethylbenzothiophen-6-yloxy)ethyl]amine;

or a salt thereof.

* * * * *